US009660198B2

(12) United States Patent
Nakagawa et al.

(10) Patent No.: US 9,660,198 B2
(45) Date of Patent: May 23, 2017

(54) ORGANIC ELECTROLUMINESCENCE ELEMENT AND COMPOUND USED THEREIN

(75) Inventors: Tetsuya Nakagawa, Fukuoka (JP); Chihaya Adachi, Fukuoka (JP); Hiroko Nomura, Fukuoka (JP); Gabor Mehes, Fukuoka (JP); Keiro Nasu, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 613 days.

(21) Appl. No.: 14/233,029

(22) PCT Filed: Jul. 13, 2012

(86) PCT No.: PCT/JP2012/067969
§ 371 (c)(1),
(2), (4) Date: Jan. 15, 2014

(87) PCT Pub. No.: WO2013/011954
PCT Pub. Date: Jan. 24, 2013

(65) Prior Publication Data
US 2014/0138670 A1 May 22, 2014

(30) Foreign Application Priority Data

Jul. 15, 2011 (JP) ................................ 2011-157029
Jan. 30, 2012 (JP) ................................ 2012-016313
Apr. 16, 2012 (JP) ................................ 2012-092585

(51) Int. Cl.
*H01L 51/00* (2006.01)
*C07D 219/02* (2006.01)
*C09K 11/06* (2006.01)
*H01L 51/50* (2006.01)
*H05B 33/10* (2006.01)

(52) U.S. Cl.
CPC ........ *H01L 51/0067* (2013.01); *C07D 219/02* (2013.01); *C09K 11/06* (2013.01); *H01L 51/0072* (2013.01); *H01L 51/5012* (2013.01); *H05B 33/10* (2013.01); *C09K 2211/1007* (2013.01); *C09K 2211/1011* (2013.01); *C09K 2211/1029* (2013.01); *H01L 2251/554* (2013.01)

(58) Field of Classification Search
CPC .................. C07D 219/02; C09K 11/06; C09K 2211/1007; C09K 2211/1011; C09K 2211/1029; H01L 51/0067; H01L 51/5012; H01L 51/0072; H01L 2251/554; H05B 33/10
See application file for complete search history.

(56) References Cited

U.S. PATENT DOCUMENTS

| 5,030,420 A | 7/1991 | Bacon |
| 2003/0168970 A1* | 9/2003 | Tominaga ............... C07C 15/28 313/504 |
| 2004/0219386 A1 | 11/2004 | Thoms |

(Continued)

FOREIGN PATENT DOCUMENTS

| CN | 101035878 A | 9/2007 |
| CN | 101659638 A | 3/2010 |

(Continued)

OTHER PUBLICATIONS

The Free Dictionary—Nitrile, pp. 1-2, no publication date given, obtained online from http://www.thefreedictionary.com/nitrile.*
The Official Action, dated Jan. 28, 2016 in corresponding Chinese Patent Application No. 201280035225.X.
European search report dated Mar. 13, 2015. issued in the corresponding European patent application No. 12815130.5-1555 / 2733762.
International preliminary report on patentability in corresponding PCT/JP2012/067969, mailed on Jul. 13, 2012.

(Continued)

*Primary Examiner* — Alexander Kollias
(74) *Attorney, Agent, or Firm* — Browdy and Neimark, PLLC

(57) ABSTRACT

An organic electroluminescence element in which a compound represented by the general formula below is used in a light-emitting layer exhibits a high emission efficiency and is inexpensive to provide. At least one of $R^1$ to $R^8$ and $R^{17}$ represent an electron-donating group and the others represent a hydrogen atom; at least one of $R^9$ to $R^{16}$ represent an electron-withdrawing group that does not have an unshared electron pair at the α-position thereof and the others represent a hydrogen atom; Z represents a single bond or $>C=Y$; Y represents O, S, $C(CN)_2$ or $C(COOH)_2$; provided that when Z is a single bond, then at least one of $R^9$ to $R^{16}$ is an electron-withdrawing group that does not have an unshared electron pair at the α-position thereof.

24 Claims, 6 Drawing Sheets

(56) References Cited

U.S. PATENT DOCUMENTS

| | | | | |
|---|---|---|---|---|
| 2007/0292715 | A1* | 12/2007 | Yoon | C07D 221/20 428/690 |
| 2008/0303434 | A1* | 12/2008 | Cho | C07D 221/20 313/506 |
| 2010/0019658 | A1 | 1/2010 | Lin et al. | |
| 2011/0198571 | A1 | 8/2011 | Huang et al. | |
| 2012/0001537 | A1 | 1/2012 | Lin et al. | |

FOREIGN PATENT DOCUMENTS

| CN | 102229565 A | 11/2011 |
|---|---|---|
| JP | H06043963 B2 | 6/1994 |
| JP | 06043963 B2 | 8/1994 |
| JP | H07278537 A | 10/1995 |
| JP | 2001509888 A | 7/2001 |
| JP | 2003149152 A | 5/2003 |
| JP | 2007278537 A | 10/2007 |
| JP | 2008096360 A | 4/2008 |
| JP | 2008281467 A | 11/2008 |
| JP | 2009203176 A | 9/2009 |
| JP | 2013253121 A | 12/2013 |
| TW | 201005070 A | 2/2010 |
| WO | 9826709 A1 | 6/1998 |
| WO | 2006033564 A1 | 3/2006 |
| WO | 2006080637 A1 | 8/2006 |
| WO | 2006080638 A1 | 8/2006 |
| WO | 2006080640 A1 | 8/2006 |
| WO | 2006080641 A1 | 8/2006 |
| WO | 2006080642 A1 | 8/2006 |
| WO | 2006080643 A1 | 8/2006 |
| WO | 2006080644 A1 | 8/2006 |
| WO | 2006080645 A1 | 8/2006 |
| WO | 2006080646 A1 | 8/2006 |
| WO | 2007105906 A1 | 9/2007 |

OTHER PUBLICATIONS

Office Action dated May 20, 2014 issued in the corresponding Japanese Patent application 2012092586.
Japanese Office Action dated Sep. 8, 2015. issued in the corresponding Chinese patent application No. 2013-524707.
The Official Action, dated Nov. 26, 2014 in the corresponding Taiwanese Patent Application No. 101125565.
Japanese Office Action dated Sep. 8, 2015, issued in the corresponding Japanese patent application No. 2013-524707.
Chinese Office Action dated Jul. 3, 2015, issued in the corresponding Chinese patent application No. 201280035225.
Wen-Yi Hung et al "An ambipolar host material provides highly efficient saturated red PhOLEDs possessing simple device structures" Physical Chemistry Chemical Physics. 10:38:5822-5825 (Jul. 2008).
Office action dated May 30, 2016, for corresponding Chinese Patent Application No. 201280035225.X.

* cited by examiner

ORGANIC ELECTROLUMINESCENCE ELEMENT AND COMPOUND USED THEREIN

TECHNICAL FIELD

The present invention relates to an organic electroluminescence element (organic EL element) having a high emission efficiency, and to a light-emitting material for use therein.

BACKGROUND ART

A lot of studies for increasing the emission efficiency of organic electroluminescence elements are being made. In particular, various kinds of efforts have been made to increase the emission efficiency by newly developing and combining an electron transport material, a hole transport material, a light-emitting materials and others that constitute an organic electroluminescence element. Among them, there are seen some studies relating to an organic electroluminescence element that utilizes an acridine structure-having spiro compound, for which some proposals have heretofore been made.

For example, PTL 1 to 4 describe organic electroluminescence elements using a compound that has a spiro-bonded acridine structure and fluorene structure, as the host material in the hole transport layer therein. Of those, PTL 1 also describes an organic electroluminescence element using a compound that has a spiro-bonded acridine structure and anthrone structure, as the host material in the hole transport layer therein. In addition, PTL 5 to 14 describe organic electroluminescence elements using a compound that has a spiro-bonded acridine structure and fluorene structure, in the light-emitting layer therein.

CITATION LIST

Patent Literature

PTL 1: CN-A 101659638
PTL 2: US-A 2004/219386
PTL 3: US-A 2010/19658
PTL 4: WO2007/105906
PTL 5: WO2006/33564
PTL 6: WO2006/80637
PTL 7: WO2006/80638
PTL 8: WO2006/80640
PTL 9: WO2006/80641
PTL 10: WO2006/80642
PTL 11: WO2006/80643
PTL 12: WO2006/80644
PTL 13: WO2006/80645
PTL 14: WO2006/80646

SUMMARY OF INVENTION

Technical Problem

As in the above, various investigations of acridine structure-having spiro compounds have heretofore been made, and some proposals relating to application of those compounds to organic electroluminescence elements have been made. However, it could not be said that comprehensive studies relating to all such acridine structure-having spiro compounds could have been achieved thoroughly. In particular, regarding use of an acridine structure-having spiro compound as a light-emitting material in an organic electroluminescence element, usefulness of only a part of such compounds has heretofore been confirmed. In addition, any definite relationship between the chemical structure of an acridine structure-having spiro compound and the usefulness of the compound as a light-emitting material could not be found out as yet, and the situation is that it is difficult to anticipate the usefulness of the compound as a light-emitting material based on the chemical structure thereof. Further, synthesis of an acridine structure-having spiro compound is not always easy, and therefore it is also difficult to provide the compound itself. Taking these problems into consideration, the present inventors synthesized acridine structure-having spiro compounds that have not as yet been developed and investigated in the art, and advanced the investigation for evaluating the usefulness of those compounds as a light-emitting material in organic electroluminescence elements. In addition, the inventors made assiduous studies for the purpose of leading out a general formula of compounds useful as a light-emitting material and generalizing the constitution of an organic electroluminescence element having a high emission efficiency.

Solution to Problem

For attaining the above-mentioned objects, the present inventors made assiduous studies and, as a result, have clarified that acridine structure-having, specific spiro compounds are useful as a light-emitting material for organic electroluminescence elements. In particular, the inventors have found out for the first time some compounds useful as a delayed fluorescence material in acridine structure-having spiro compounds, and have clarified the possibility of inexpensively providing an organic electroluminescence element having a high emission efficiency. Based on these findings, the present inventors have provided the present invention described hereinunder, as a solution to the above problems.

[1] An organic electroluminescence element having an anode, a cathode, and at least one organic layer containing a light-emitting layer between the anode and the cathode, wherein the light-emitting layer contains a compound represented by the following general formula (1):

[Chem. 1]

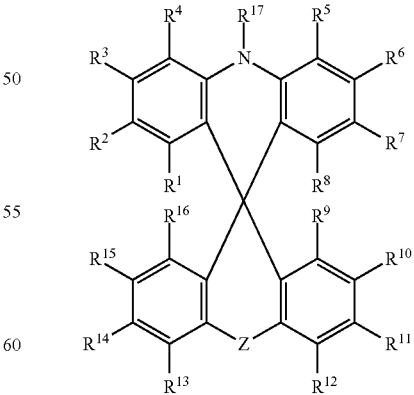

General Formula (1)

In the general formula (1), $R^1$, $R^2$, $R^3$, $R^4$, $R^5$, $R^6$, $R^7$, $R^8$ and $R^{17}$ each independently represent a hydrogen atom or an electron-donating group, and at least one of these is an electron-donating group. $R^9$, $R^{10}$, $R^{11}$, $R^{12}$, $R^{13}$, $R^{14}$, $R^{15}$, and R¹⁶ each independently represent a hydrogen atom, or an electron-withdrawing group that does not have an unshared electron pair at the α-position thereof. Z represents a single bond or >C=Y, Y represents O, S, C(CN)₂ or C(COOH)₂. However, when Z is a single bond, then at least one of R⁹, R¹⁰, R¹¹, R¹², R¹³, R¹⁴, R¹⁵ and R¹⁶ is an electron-withdrawing group that does not have an unshared electron pair at the α-position thereof.

[2] The organic electroluminescence element according to [1], which radiates delayed fluorescence.

[3] The organic electroluminescence element according to [1] or [2], wherein Z in the general formula (1) is a single bond.

[4] The organic electroluminescence element according to [1] or [2], wherein Z in the general formula (1) is a carbonyl group.

[5] The organic electroluminescence element according to [1] or [2], wherein Z in the general formula (1) is >C=C(CN)₂.

[6] The organic electroluminescence element according to any one of [1] to [5], wherein R¹⁷ in the general formula (1) is an aryl group.

[7] The organic electroluminescence element according to any one of [1] to [6], wherein at least one of R¹, R², R³, R⁴, R⁵, R⁶, R⁷ and R⁸ in the general formula (1) is an aryl group substituted with an electron-donating group.

[8] The organic electroluminescence element according to any one of [1] to [6], wherein at least one of R¹, R², R³, R⁴, R⁵, R⁶, R⁷ and R⁸ in the general formula (1) has a structure represented by the following general formula (2):

[Chem. 2]

General Formula (2)

In the general formula (2), R²¹, R²², R²³, R²⁴ and R²⁵ each independently represent a hydrogen atom or an electron-donating group, and at least one of these is an electron-donating group.

[9] The organic electroluminescence element according to any one of [1] to [6], wherein at least one of R¹, R², R³, R⁴, R⁵, R⁶, R⁷ and R⁸ in the general formula (1) has a structure represented by any of the following general formulae (3) to (5):

[Chem. 3]

General Formula (3)

General Formula (4)

General Formula (5)

In the above formulae, R³¹ and R³² each independently represent a substituted or unsubstituted aryl group; and the aryl group represented by R³¹ may bond to the aryl group represented by R³². R⁴¹, R⁴² and R⁴³ each independently represent a hydrogen atom, a substituted or unsubstituted alkyl group, or a substituted or unsubstituted aryl group; R⁴¹ and R⁴² may together form a cyclic structure, and R⁴² and R⁴³ may together form a cyclic structure. R⁵¹, R⁵² and R⁵³ each independently represent a hydrogen atom, a substituted or unsubstituted alkyl group, or a substituted or unsubstituted aryl group; R⁵¹ and R⁵² may together form a cyclic structure, and R⁵² and R⁵³ may together form a cyclic structure.

[10] The organic electroluminescence element according to any one of [1] to [6], wherein at least one of R¹, R², R³, R⁴, R⁵, R⁶, R⁷ and R⁸ in the general formula (1) has any of the following structures:

[Chem. 4]

[11] The organic electroluminescence element according to any one of [1] to [10], wherein at least one of R⁹, R¹⁰, R¹¹, R¹², R¹³, R¹⁴, R¹⁵, and R¹⁶ is a cyano group or has a structure represented, by any of the following general formulae (6) to (9):

[Chem. 5]

General Formula (6)

General Formula (7)

-continued

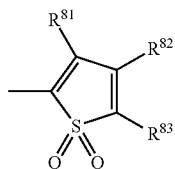
General Formula (8)

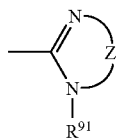
General Formula (9)

In the above formulae, $R^{61}$ and $R^{62}$ each independently represent a substituted or unsubstituted aryl group. $R^{71}$ and $R^{72}$ each independently represent a hydrogen atom, a substituted or unsubstituted alkyl group, or a substituted or unsubstituted aryl group; and $R^{71}$ and $R^{72}$ may together form a cyclic structure. $R^{81}$, $R^{82}$ and $R^{83}$ each independently represent a hydrogen atom, a substituted or unsubstituted alkyl group, or a substituted or unsubstituted aryl group; $R^{81}$ and $R^{82}$ may together form a cyclic structure, and $R^{82}$ and $R^{83}$ may together form a cyclic structure. $R^{91}$ represents a hydrogen atom, a substituted or unsubstituted alkyl group, or a substituted or unsubstituted aryl group; and Z represents a linking group necessary for forming a heteroaromatic ring.

[12] The organic electroluminescence element according to any one of [1] to [10], wherein at least one of $R^9$, $R^{10}$, $R^{11}$, $R^{12}$, $R^{13}$, $R^{14}$, $R^{15}$ and $R^{16}$ in the general formula (1) has any of the following structures:

[Chem. 6]

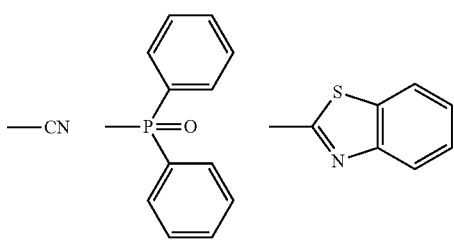

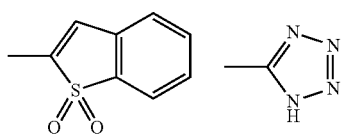

[13] The organic electroluminescence element according to any one of [1] to [12], wherein the compound represented by the general formula (1) is used as the dopant in the light-emitting layer.

[14] A compound represented by the following general formula (1'):

[Chem. 7]

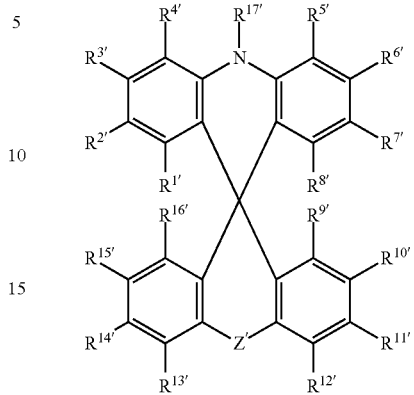
General Formula (1')

In the general formula (1'), $R^{1'}$, $R^{2'}$, $R^{3'}$, $R^{4'}$, $R^{5'}$, $R^{6'}$, $R^{7'}$, $R^{8'}$ and $R^{17'}$ each independently represent a hydrogen atom or an electron-donating group, and at least one of these is an electron-donating group. $R^{9'}$, $R^{10'}$, $R^{11'}$, $R^{12'}$, $R^{13'}$, $R^{14'}$, $R^{15'}$ and $R^{16'}$ each independently represent a hydrogen atom or a cyano group. Z' represents a single bond or >C=Y, Y represents O, S, C(CN)$_2$ or C(COOH)$_2$. However, when Z' is a single bond, >C=O or >C=S, then at least one of $R^{9'}$, $R^{10'}$, $R^{11'}$, $R^{12'}$, $R^{13'}$, $R^{14'}$, $R^{15'}$ and $R^{16'}$ is a cyano group.

[15] The compound according to [14], wherein Z' in the general formula (1') is a single bond.

[16] The compound according to [14], wherein Z' in the general formula (1') is a carbonyl group.

[17] The compound according to [14] wherein Z' in the general formula (1') is >C=C(CN)$_2$.

[18] The compound according to any one of [14] to [17], wherein $R^{17'}$ in the general formula (1') is an aryl group.

[19] The compound according to any one of [14] to [17], wherein at least one of $R^{1'}$, $R^{2'}$, $R^{3'}$, $R^{4'}$, $R^{5'}$, $R^{6'}$, $R^{7'}$ and $R^{8'}$ in the general formula (1') is an aryl group substituted with an electron-donating group.

[20] The compound according to any one of [14] to [17], wherein at least one of $R^{1'}$, $R^{2'}$, $R^{3'}$, $R^{4'}$, $R^{5'}$, $R^{6'}$, $R^{7'}$ and $R^{8'}$ in the general formula (1') has a structure represented by the following general formula (2):

[Chem. 8]

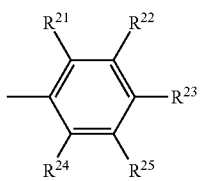
General Formula (2)

In the general formula (2), $R^{21}$, $R^{22}$, $R^{23}$, $R^{24}$ and $R^{25}$ each independently represent a hydrogen atom or an electron-donating group, and at least one of these is an electron-donating group.

[21] The compound according to any one of [14] to [17], wherein at least one of $R^{1'}$, $R^{2'}$, $R^{3'}$, $R^{4'}$, $R^{5'}$, $R^{6'}$, $R^{7'}$ and $R^{8'}$ in the general formula (1') has a structure represented by any of the following general formulae (3) to (5):

[Chem. 9]

General Formula (3)

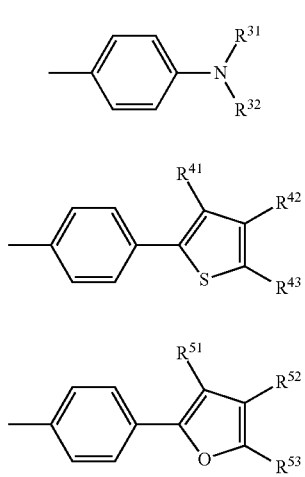

General Formula (4)

General Formula (5)

In the above formulae, $R^{31}$ and $R^{32}$ each independently represent a substituted or unsubstituted aryl group; and the aryl group represented by $R^{31}$ may bond to the aryl group represented by $R^{32}$. $R^{41}$, $R^{42}$ and $R^{43}$ each independently represent a hydrogen atom, a substituted or unsubstituted alkyl group, or a substituted or unsubstituted aryl group; $R^{41}$ and $R^{42}$ may together form a cyclic structure, and $R^{42}$ and $R^{43}$ may together form a cyclic structure. $R^{51}$, $R^{52}$ and $R^{53}$ each independently represent a hydrogen atom, a substituted or unsubstituted alkyl group, or a substituted or unsubstituted aryl group; $R^{51}$ and $R^{52}$ may together form a cyclic structure, and $R^{52}$ and $R^{53}$ may together form a cyclic structure.

[22] The compound according to any one of [14] to [17], wherein at least one of $R^{1'}$, $R^{2'}$, $R^{3'}$, $R^{4'}$, $R^{5'}$, $R^{6'}$, $R^{7'}$ and $R^{8'}$ in the general formula (1') has any of the following structures:

[Chem. 10]

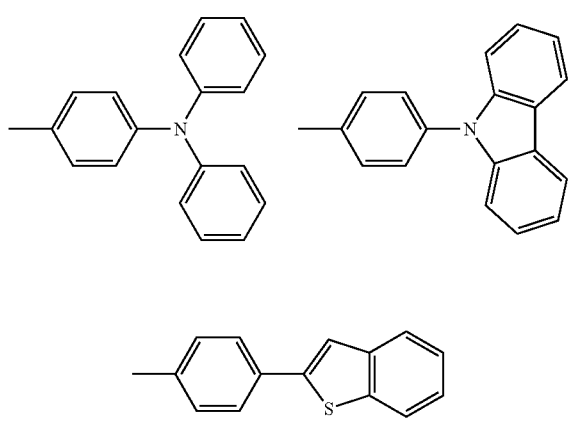

[23] A delayed fluorescence material comprising a compound represented by the following general formula (1):

[Chem. 11]

General Formula (1)

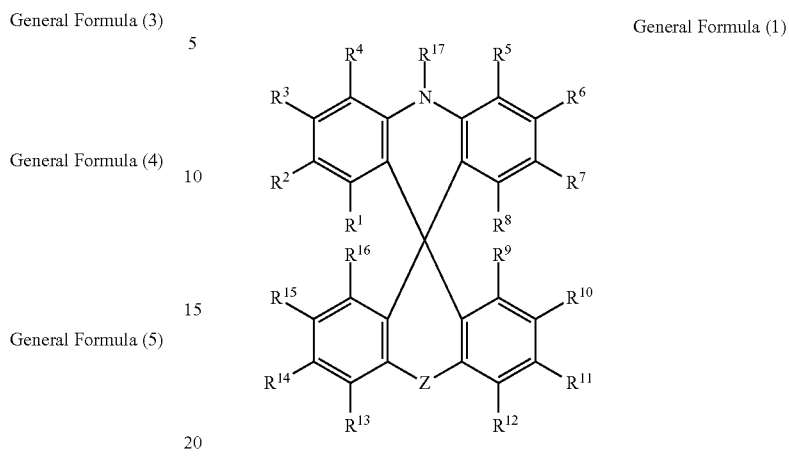

In the general formula (1), $R^1$, $R^2$, $R^3$, $R^4$, $R^5$, $R^6$, $R^7$, $R^8$ and $R^{17}$ each independently represent a hydrogen atom or an electron-donating group, and at least one of these is an electron-donating group. $R^9$, $R^{10}$, $R^{11}$, $R^{12}$, $R^{13}$, $R^{14}$, $R^{15}$ and $R^{16}$ each independently represent a hydrogen atom, or an electron-withdrawing group that does not have an unshared electron pair at the α-position thereof. Z represents a single bond or >C=Y, Y represents O, S, C(CN)$_2$ or C(COOH)$_2$. However, when Z is a single bond, then at least one of $R^9$, $R^{10}$, $R^{11}$, $R^{12}$, $R^{13}$, $R^{14}$, $R^{15}$ and $R^{16}$ is an electron-withdrawing group that does not have an unshared electron pair at the α-position thereof.

[24] A delayed fluorescence material comprising a compound represented by the following general formula (1'):

[Chem. 12]

General Formula (1')

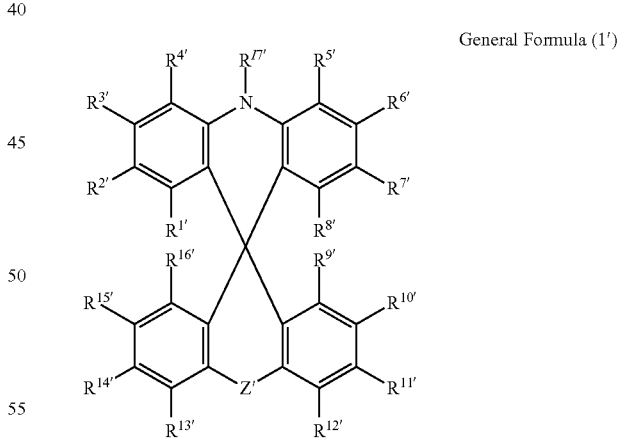

In the general formula (1'), $R^{1'}$, $R^{2'}$, $R^{3'}$, $R^{4'}$, $R^{5'}$, $R^{6'}$, $R^{7'}$, $R^{8'}$ and $R^{17'}$ each independently represent a hydrogen atom or an electron-donating group, and at least one of these is an electron-donating group. $R^{9'}$, $R^{10'}$, $R^{11'}$, $R^{12'}$, $R^{13'}$, $R^{14'}$, $R^{15'}$ and $R^{16'}$ each independently represent a hydrogen atom or a cyano group. Z' represents a single bond or >C=Y, Y represents O, S, C(CN)$_2$ or C(COOH)$_2$. However, when Z' is a single bond, >C=O or >C=S, then at least one of $R^{9'}$, $R^{10'}$, $R^{11'}$, $R^{12'}$, $R^{13'}$, $R^{14'}$, $R^{15'}$ and $R^{16'}$ is a cyano group.

Advantageous Effects of Invention

The organic electroluminescence element of the invention exhibits a high emission efficiency and is inexpensive to provide. The compound of the invention is extremely useful as the light-emitting material for such an organic electroluminescence element.

DESCRIPTION OF EMBODIMENTS

Figure 1:
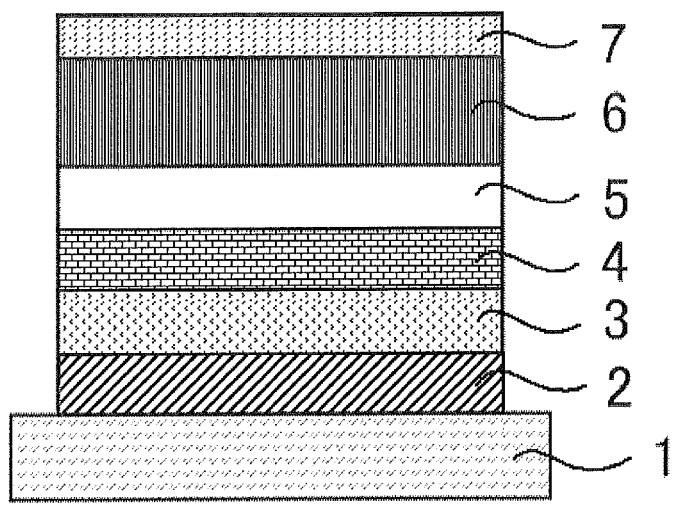
FIG. 1 This is a schematic cross-sectional view showing a layer configuration of the organic electroluminescence element of Example 1.

The contents of the invention are described in detail hereinunder. The description of the constitutive elements of the invention given hereinunder is for some typical embodiments and specific examples of the invention; however, the invention should not be limited to such embodiments and specific examples. In this description, the numerical range expressed by the wording "a number to another number" means the range that falls between the former number indicating the lower limit of the range and the latter number indicating the upper limit thereof.

[Compound Represented by General Formula (1)]

The organic electroluminescence element of the invention contains a compound represented by the following general formula (1) in the light-emitting layer therein. The compound represented by the general formula (1) is first described.

[Chem. 13]

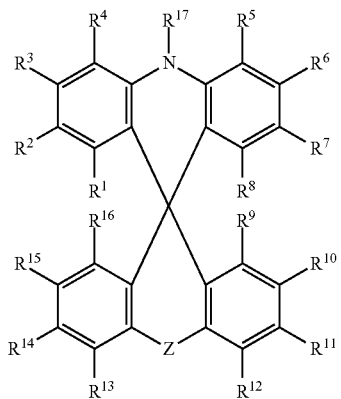

General Formula (1)

In the general formula (1), $R^1$, $R^2$, $R^3$, $R^4$, $R^5$, $R^6$, $R^7$, $R^8$ and $R^{17}$ each independently represent a hydrogen atom or an electron-donating group, and at least one of these is an electron-donating group. When two or more of these are electron-donating groups, those two or more electron-donating groups may be the same or different. Preferably, they are the same. Of $R^1$, $R^2$, $R^3$, $R^4$, $R^5$, $R^6$, $R^7$ and $R^8$ and $R^{17}$, preferably, any of $R^2$, $R^3$, $R^4$, $R^5$, $R^6$, $R^7$ and $R^{17}$ is an electron-donating group, and more preferably, any of $R^2$, $R^3$, $R^6$, $R^7$ and $R^{17}$ is an electron-donating group. Even more preferably, $R^{17}$ is an electron-donating group, or any one or two of $R^2$, $R^3$, $R^6$ and $R^7$ each are an electron-donating group. In case where two of those are electron-donating groups, preferably, any one of $R^2$ and $R^3$ and any one of $R^6$ and $R^7$ each are an electron-donating group.

The electron-donating group represented by $R^1$, $R^2$, $R^3$, $R^4$, $R^5$, $R^6$, $R^7$, $R^8$ and $R^{17}$ is a group which, when bonding to the spiro ring, exhibits a property of donating an electron to the ring. The electron-donating group may be any of an aromatic group, a heteroaromatic group or an aliphatic group, or may be a composite group formed of two or more of these groups. Examples of the electron-donating group include an alkyl group (which may be any of a linear, branched or cyclic group, preferably having from 1 to 6 carbon atoms, more preferably from 1 to 3 carbon atoms, and concretely includes a methyl group, an ethyl group, a propyl group, a pentyl group, a hexyl group, an isopropyl group), an alkoxy group (which may be any of a linear, branched or cyclic group, preferably having from 1 to 6 carbon atoms, more preferably from 1 to 3 carbon atoms, and concretely includes a methoxy group), an amino group or a substituted amino group (preferably an amino group substituted with an aromatic group, concretely including a diphenylamino group, an anilyl group, a tolylamino group), an aryl group (which may be a single ring or a fused ring and may be further substituted with an aryl group, concretely including a phenyl group, a biphenyl group, a terphenyl group), an electron-donating group that contains a heterocyclic structure (preferably an electron-donating group that contains a heterocyclic structure containing a nitrogen atom or a sulfur atom, concretely including a thiophenyl group, a benzothiophenyl group, a julolidyl group, a pyrrolyl group, an indolyl group, a carbazolyl group), etc. Preferably, for example, the electron-donating group has a σp value of at most −0.06, more preferably at most −0.14, even more preferably at most −0.28.

Of those, preferably, $R^1$, $R^2$, $R^3$, $R^4$, $R^5$, $R^6$, $R^7$ and $R^8$ each are a hydrogen atom or an aryl group substituted with an electron-donating group. The aryl group may comprise one aromatic ring or may have a fused structure of two or more aromatic rings. Preferably, the carbon number of the aryl group is from 6 to 22, more preferably from 6 to 18, even more preferably from 6 to 14, still more preferably from 6 to 10 (i.e., a phenyl group, a 1-naphthyl group, a 2-naphthyl group), most preferably a phenyl group. The electron-donating group to be a substituent on the aryl group is preferably one having the above-mentioned σp value.

More preferably, $R^1$, $R^2$, $R^3$, $R^4$, $R^5$, $R^6$, $R^7$ and $R^8$ each are a hydrogen atom or a group represented by the following general formula (2):

[Chem. 14]

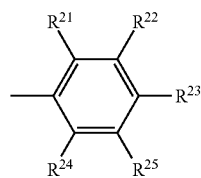

General Formula (2)

In the general formula (2), $R^{21}$, $R^{22}$, $R^{23}$, $R^{24}$ and $R^{25}$ each independently represent a hydrogen atom or an electron-donating group, and at least one of these is an electron-donating group. The electron-donating group is preferably one having the above-mentioned σp value. Among $R^{21}$, $R^{22}$, $R^{23}$, $R^{24}$ and $R^{25}$, preferably, $R^{22}$ and $R^{24}$ each are an electron-donating group, or $R^{23}$ is an electron-donating group, and more preferably, $R^{23}$ is an electron-donating group.

More preferably, $R^1$, $R^2$, $R^3$, $R^4$, $R^5$, $R^6$, $R^7$ and $R^8$ each are a hydrogen atom or have a structure represented by any of the following general formulae (3) to (5):

[Chem. 13]

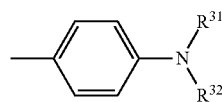

General Formula (3)

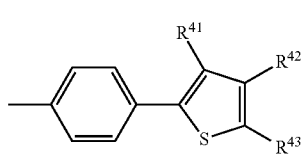

General Formula (4)

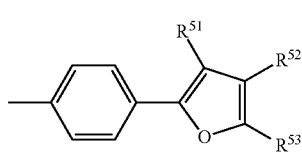

General Formula (5)

In the above formulae, $R^{31}$ and $R^{32}$ each independently represent a substituted or unsubstituted aryl group; and the aryl group represented by $R^{31}$ may bond to the aryl group represented by $R^{32}$. $R^{41}$, $R^{42}$ and $R^{43}$ each independently represent a hydrogen atom, a substituted or unsubstituted alkyl group, or a substituted or unsubstituted aryl group; $R^{41}$ and $R^{42}$ may together form a cyclic structure, and $R^{42}$ and $R^{43}$ may together form a cyclic structure. $R^{51}$, $R^{52}$ and $R^{53}$ each independently represent a hydrogen atom, a substituted or unsubstituted alkyl group, or a substituted or unsubstituted aryl group; $R^{51}$ and $R^{52}$ may together form a cyclic structure, and $R^{52}$ and $R^{53}$ may together form a cyclic structure.

The cyclic structure to be formed together by $R^{41}$ and $R^{42}$, by $R^{42}$ and $R^{43}$, by $R^{51}$ and $R^{52}$, as well as by $R^{52}$ and $R^{53}$ may be any of an aromatic ring, a heteroaromatic ring or an aliphatic ring, but is preferably an aromatic ring or a heteroaromatic ring, more preferably an aromatic ring. Specific examples of the cyclic structure include a benzene ring, a naphthalene ring, an anthracene ring, a phenanthrene ring, etc.

The aryl group as referred to in this description may comprise one aromatic ring or may have a fused structure of two or more aromatic rings. Preferably, the carbon number of the aryl group is from 6 to 22, more preferably from 6 to 18, even more preferably from 6 to 14, still more preferably from 6 to 10 (i.e., a phenyl group, a 1-naphthyl group, a 2-naphthyl group).

The alkyl group as referred to in this description may be linear, branched or cyclic. Preferred is a linear or branched alkyl group. The carbon number of the alkyl group is preferably from 1 to 20, more preferably from 1 to 12, even more preferably from 1 to 6, still more preferably from 1 to 3 (i.e., a methyl group, an ethyl group, an n-propyl group, an isopropyl group). The cyclic alkyl group includes, for example, a cyclopentyl group, a cyclohexyl group, a cycloheptyl group.

The substituent for the aryl group and the alkyl group includes an alkyl group, an aryl group, an alkoxy group, an aryloxy group. The description and the preferred range of the alkyl group and the aryl group that may be employed here as the substituent are the same as mentioned above. The alkoxy group that may be employed as the substituent may be linear, branched or cyclic. Preferred is a linear or branched alkoxy group. The carbon number of the alkoxy group is preferably from 1 to 20, more preferably from 1 to 12, even more preferably from 1 to 6, still more preferably from 1 to 3 (i.e., a methoxy group, an ethoxy group, an n-propoxy group, an isopropoxy group). The cyclic alkoxy group includes, for example, a cyclopentyloxy group, a cyclohexyloxy group, a cycloheptyloxy group. The aryloxy group that may be employed here as the substituent may comprise one aromatic ring or may have a fused structure of two or more aromatic rings. The carbon number of the aryloxy group is preferably from 6 to 22, more preferably from 6 to 18, even more preferably from 6 to 14, still more preferably from 6 to 10 (i.e., a phenyloxy group, a 1-naphthyloxy group, a 2-naphthyloxy group).

As the substituent for the alkyl group and the aryl group in the general formulae (3) to (5), further mentioned is an electron-donating group.

Preferred examples of the electron-donating group to be represented by $R^1$, $R^2$, $R^3$, $R^4$, $R^5$, $R^6$, $R^7$ and $R^8$ are mentioned below. However, the electron-donating group that may be employed in the general formula (1) should not be limitatively interpreted by these specific examples.

(Chem. 16)

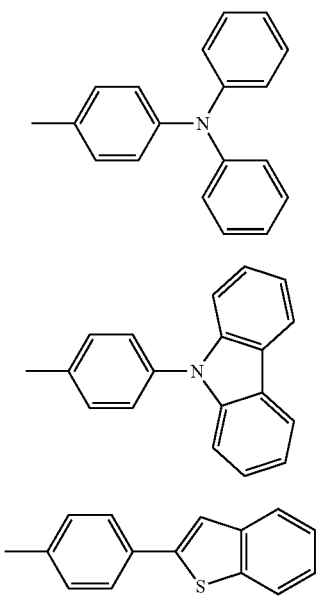

R$^9$, R$^{10}$, R$^{11}$, R$^{12}$, R$^{13}$, R$^{14}$, R$^{15}$ and R$^{16}$ in the general formula (1) each independently represent a hydrogen atom, or an electron-withdrawing group that does not have an unshared electron pair at the α-position thereof. However, when Z is a single bond, then at least one of these is an electron-withdrawing group that does not have an unshared electron pair at the α-position thereof. When two or more of these each are an electron-withdrawing group, the two or more electron-withdrawing groups may be the same or different. Preferably, they are the same. Of R$^9$, R$^{10}$, R$^{11}$, R$^{12}$, R$^{13}$, R$^{14}$, R$^{15}$ and R$^{16}$, preferably, any of R$^{10}$, R$^{11}$, R$^{12}$, R$^{13}$, R$^{14}$ and R$^{15}$ is an electron-withdrawing group, more preferably any of R$^{10}$, R$^{11}$, R$^{14}$ and R$^{15}$ is an electron-withdrawing group. Even more preferably, one or two of R$^{10}$, R$^{11}$, R$^{14}$ and R$^{15}$ each are an electron-withdrawing group. When two are electron-withdrawing groups, preferably, any one of R$^{10}$ and R$^{11}$ and any one of R$^{14}$ and R$^{15}$ are electron-withdrawing groups.

The electron-withdrawing group to be represented by R$^9$, R$^{10}$, R$^{11}$, R$^{12}$, R$^{13}$, R$^{14}$, R$^{15}$ and R$^{16}$ in the general formula (1) is a group which, when bonding to the spiro ring, exhibits a property of withdrawing an electron from the spiro ring. However, an electron-withdrawing group that has an unshared electron pair at the α-position thereof (for example, halogen atom) is excluded here. The electron-withdrawing group may be any of an aromatic group, a heteroaromatic group or an aliphatic group, or may be a composite group formed of two or more of these groups. Examples of the electron-withdrawing group include a nitro group, a perfluoroalkyl group (preferably having from 1 to 6 carbon atoms, more preferably from 1 to 3 carbon atoms, and concretely including a trifluoromethyl group), a sulfonyl group, an electron-withdrawing group that has a heterocyclic structure (preferably an electron-withdrawing group that contains a heterocyclic structure containing a nitrogen atom or a sulfur atom, concretely including an oxadiazolyl group, a benzothiadiazolyl group, a tetrazolyl group, a thiazolyl group, an imidazolyl group, etc.), a phosphine oxide structure-containing group, a cyano group, etc. The family of the electron-withdrawing group includes, for example, those of the examples of the electron-withdrawing group mentioned above except the cyano group. Preferably, the electron-withdrawing group has, for example, a σp value of at least 0.02, more preferably at least 0.34, even more preferably at least 0.62.

Preferably, at least one of R$^9$, R$^{10}$, R$^{11}$, R$^{12}$, R$^{13}$, R$^{14}$, R$^{15}$ and R$^{16}$ is a cyano group, or has a structure of any of the following general formulae (6) to (9):

[Chem. 17]

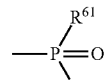

General Formula (6)

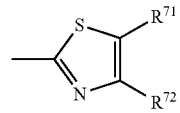

General Formula (7)

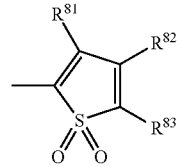

General Formula (8)

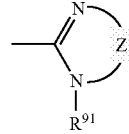

General Formula (9)

In the above formulae, R$^{61}$ and R$^{62}$ each independently represent a substituted or unsubstituted aryl group. R$^{71}$ and R$^{72}$ each independently represent a hydrogen atom, a substituted or unsubstituted alkyl group, or a substituted or unsubstituted aryl group; and R$^{71}$ and R$^{72}$ may together form a cyclic structure. R$^{81}$, R$^{82}$ and R$^{83}$ each independently represent a hydrogen atom, a substituted or unsubstituted alkyl group, or a substituted or unsubstituted aryl group; R$^{81}$ and R$^{82}$ may together form a cyclic structure, and R$^{82}$ and R$^{83}$ may together form a cyclic structure. R$^{91}$ represents a hydrogen atom, a substituted or unsubstituted alkyl group, or a substituted or unsubstituted aryl group; and Z represents a linking group necessary for forming a heteroaromatic ring. The linking chain of Z may be one comprising carbon atoms alone, or may be one comprising hetero atoms alone, or may be one comprising carbon atoms and hetero atoms in mixture. The hetero atom is preferably a nitrogen atom. Preferably, the linking chain has a 2- to 4-atom length, more preferably a 2- or 3-atom length.

For the description and the preferred range of the aryl group and the aryl group as referred to herein, referred to are the description and the preferred range of the aryl group and the alkyl group which R$^{41}$, R$^{42}$, R$^{43}$, R$^{51}$, R$^{52}$ and R$^{53}$ may take. However, as the substituent for the aryl group and the alkyl group in the general formulae (6) to (9), there may be additionally mentioned an electron-withdrawing group in addition to the alkyl group, the aryl group, the alkyloxy group and the aryloxy group.

Preferred examples of the electron-withdrawing group to be represented by R$^9$, R$^{10}$, R$^{11}$, R$^{12}$, R$^{13}$, R$^{14}$, R$^{15}$ and R$^{16}$ are listed below. However, the electron-withdrawing group that may be employed in the general formula (1) should not be limitatively interpreted by these specific examples.

[Chem. 18]

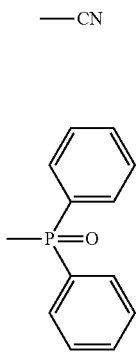

A1

A2

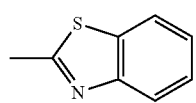

A3

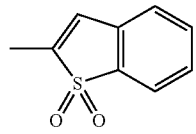

A4

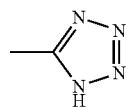

A5

$R^{17}$ in the general formula (1) represents a hydrogen atom or an electron-donating group, and for the electron-donating group of $R^{17}$, referred to are the description and the preferred range of the electron-donating group for the above-mentioned $R^1$, $R^2$, $R^3$, $R^4$, $R^5$, $R^6$, $R^7$ and $R^8$. However, the electron-donating group of $R^{17}$ is also preferably an unsubstituted aryl group, and among this, the group is more preferably an unsubstituted phenyl group. The electron-donating group of $R^{17}$ may be the same as the electron-donating group in $R^1$, $R^2$, $R^3$, $R^4$, $R^5$, $R^6$, $R^7$ and $R^8$.

In the general formula (1), Z represents a single bond or >C=Y, and Y represents O, S, C(CN)$_2$ or C(COOH)$_2$. For example, when Y is O, Z in the general formula (1) is a carbonyl group. From the viewpoint of emission efficiency, for example, more preferred are a group of compounds where $R^{17}$ is an aryl group and Z is a carbonyl group or >C=C(CN)$_2$.

Of the compounds represented by the above-mentioned general formula (1), those represented by the following general formula (1') are novel compounds.

[Chem. 19]

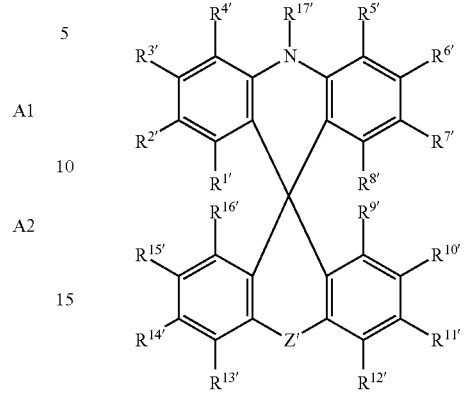

General Formula (1')

In the general formula (1'), $R^{1'}$, $R^{2'}$, $R^{3'}$, $R^{4'}$, $R^{5'}$, $R^{6'}$, $R^{7'}$, $R^{8'}$ and $R^{17'}$ each independently represent a hydrogen atom or an electron-donating group, and at least one of these is an electron-donating group. $R^{9'}$, $R^{10'}$, $R^{11'}$, $R^{12'}$, $R^{13'}$, $R^{14'}$, $R^{15'}$ and $R^{16'}$ each independently represent a hydrogen atom or a cyano group. Z' represents a single bond or >C=Y, Y represents O, S, C(CN)$_2$ or C(COOH)$_2$. When Z' is a single bond, >C=O or >C=S, then at least one of $R^{9'}$, $R^{10'}$, $R^{11'}$, $R^{12'}$, $R^{13'}$, $R^{14'}$, $R^{15'}$ and $R^{16'}$ is a cyano group.

For the description and the preferred range of the electron-donating group and the electron-withdrawing group in the general formula (1'), referred to are the corresponding descriptions in the general formula (1) mentioned above.

The molecular weight of the compound represented by the general formula (1) is, for example, when an organic layer containing the compound is intended to be formed through vapor deposition in use thereof, preferably at most 1500, more preferably at most 1200, even more preferably at most 1000, still more preferably at most 800. The lower limit of the molecular weight may be, for example, at least 350.

Specific examples of the compound represented by the general formula (1) are shown below. However, the compound represented by the general formula (1) for use in the invention should not be limitatively interpreted by these specific examples. In the Tables, D1 to D3 each represent an aryl group substituted with the above-mentioned electron-donating group; A1 to A5 each represent the above-mentioned electron-withdrawing group; H represents a hydrogen atom; and Ph represents a phenyl group.

TABLE 1

| Compound No. | $R^2$ | $R^7$ | $R^{10}$ | $R^{15}$ | $R^{17}$ | Z | Other R |
|---|---|---|---|---|---|---|---|
| 1 | H | H | A1 | A1 | Ph | single bond | H |
| 2 | H | D1 | A1 | A1 | Ph | single bond | H |
| 3 | H | D2 | A1 | A1 | Ph | single bond | H |
| 4 | H | D3 | A1 | A1 | Ph | single bond | H |
| 5 | H | H | A2 | A2 | Ph | single bond | H |
| 6 | H | D1 | A2 | A2 | Ph | single bond | H |
| 7 | H | D2 | A2 | A2 | Ph | single bond | H |
| 8 | H | D3 | A2 | A2 | Ph | single bond | H |
| 9 | H | H | A3 | A3 | Ph | single bond | H |
| 10 | H | D1 | A3 | A3 | Ph | single bond | H |
| 11 | H | D2 | A3 | A3 | Ph | single bond | H |
| 12 | H | D3 | A3 | A3 | Ph | single bond | H |
| 13 | H | H | A4 | A4 | Ph | single bond | H |
| 14 | H | D1 | A4 | A4 | Ph | single bond | H |
| 15 | H | D2 | A4 | A4 | Ph | single bond | H |
| 16 | H | D3 | A4 | A4 | Ph | single bond | H |
| 17 | H | H | A5 | A5 | Ph | single bond | H |

TABLE 1-continued

| Compound No. | $R^2$ | $R^7$ | $R^{10}$ | $R^{15}$ | $R^{17}$ | Z | Other R |
|---|---|---|---|---|---|---|---|
| 18 | H | D1 | A5 | A5 | Ph | single bond | H |
| 19 | H | D2 | A5 | A5 | Ph | single bond | H |
| 20 | H | D3 | A5 | A5 | Ph | single bond | H |
| 21 | D1 | D1 | A1 | A1 | Ph | single bond | H |
| 22 | D2 | D2 | A1 | A1 | Ph | single bond | H |
| 23 | D3 | D3 | A1 | A1 | Ph | single bond | H |
| 24 | D1 | D1 | A2 | A2 | Ph | single bond | H |
| 25 | D2 | D2 | A2 | A2 | Ph | single bond | H |
| 26 | D3 | D3 | A2 | A2 | Ph | single bond | H |
| 27 | D1 | D1 | A3 | A3 | Ph | single bond | H |
| 28 | D2 | D2 | A3 | A3 | Ph | single bond | H |
| 29 | D3 | D3 | A3 | A3 | Ph | single bond | H |
| 30 | D1 | D1 | A4 | A4 | Ph | single bond | H |
| 31 | D2 | D2 | A4 | A4 | Ph | single bond | H |
| 32 | D3 | D3 | A4 | A4 | Ph | single bond | H |
| 33 | D1 | D1 | A5 | A5 | Ph | single bond | H |
| 34 | D2 | D2 | A5 | A5 | Ph | single bond | H |
| 35 | D3 | D3 | A5 | A5 | Ph | single bond | H |

TABLE 2

| Compound No. | $R^3$ | $R^6$ | $R^{11}$ | $R^{14}$ | $R^{17}$ | Z | Other R |
|---|---|---|---|---|---|---|---|
| 36 | H | H | H | A1 | Ph | single bond | H |
| 37 | H | D1 | H | A1 | Ph | single bond | H |
| 38 | H | D2 | H | A1 | Ph | single bond | H |
| 39 | H | D3 | H | A1 | Ph | single bond | H |
| 40 | H | H | H | A2 | Ph | single bond | H |
| 41 | H | D1 | H | A2 | Ph | single bond | H |
| 42 | H | D2 | H | A2 | Ph | single bond | H |
| 43 | H | D3 | H | A2 | Ph | single bond | H |
| 44 | H | H | H | A3 | Ph | single bond | H |
| 45 | H | D1 | H | A3 | Ph | single bond | H |
| 46 | H | D2 | H | A3 | Ph | single bond | H |
| 47 | H | D3 | H | A3 | Ph | single bond | H |
| 48 | H | H | H | A4 | Ph | single bond | H |
| 49 | H | D1 | H | A4 | Ph | single bond | H |
| 50 | H | D2 | H | A4 | Ph | single bond | H |
| 51 | H | D3 | H | A4 | Ph | single bond | H |
| 52 | H | H | H | A5 | Ph | single bond | H |
| 53 | H | D1 | H | A5 | Ph | single bond | H |
| 54 | H | D2 | H | A5 | Ph | single bond | H |
| 55 | H | D3 | H | A5 | Ph | single bond | H |
| 56 | D1 | D1 | H | A1 | Ph | single bond | H |
| 57 | D2 | D2 | H | A1 | Ph | single bond | H |
| 58 | D3 | D3 | H | A1 | Ph | single bond | H |
| 59 | D1 | D1 | H | A2 | Ph | single bond | H |
| 60 | D2 | D2 | H | A2 | Ph | single bond | H |
| 61 | D3 | D3 | H | A2 | Ph | single bond | H |
| 62 | D1 | D1 | H | A3 | Ph | single bond | H |
| 63 | D2 | D2 | H | A3 | Ph | single bond | H |
| 64 | D3 | D3 | H | A3 | Ph | single bond | H |
| 65 | D1 | D1 | H | A4 | Ph | single bond | H |
| 66 | D2 | D2 | H | A4 | Ph | single bond | H |
| 67 | D3 | D3 | H | A4 | Ph | single bond | H |
| 68 | D1 | D1 | H | A5 | Ph | single bond | H |
| 69 | D2 | D2 | H | A5 | Ph | single bond | H |
| 70 | D3 | D3 | H | A5 | Ph | single bond | H |

TABLE 3

| Compound No. | $R^2$ | $R^7$ | $R^{10}$ | $R^{15}$ | $R^{17}$ | Z | Other R |
|---|---|---|---|---|---|---|---|
| 71 | H | H | A1 | A1 | Ph | C=O | H |
| 72 | H | D1 | A1 | A1 | Ph | C=O | H |
| 73 | H | D2 | A1 | A1 | Ph | C=O | H |
| 74 | H | D3 | A1 | A1 | Ph | C=O | H |
| 75 | H | H | A2 | A2 | Ph | C=O | H |
| 76 | H | D1 | A2 | A2 | Ph | C=O | H |
| 77 | H | D2 | A2 | A2 | Ph | C=O | H |
| 78 | H | D3 | A2 | A2 | Ph | C=O | H |
| 79 | H | H | A3 | A3 | Ph | C=O | H |
| 80 | H | D1 | A3 | A3 | Ph | C=O | H |
| 81 | H | D2 | A3 | A3 | Ph | C=O | H |
| 82 | H | D3 | A3 | A3 | Ph | C=O | H |
| 83 | H | H | A4 | A4 | Ph | C=O | H |
| 84 | H | D1 | A4 | A4 | Ph | C=O | H |
| 85 | H | D2 | A4 | A4 | Ph | C=O | H |
| 86 | H | D3 | A4 | A4 | Ph | C=O | H |
| 87 | H | H | A5 | A5 | Ph | C=O | H |
| 88 | H | D1 | A5 | A5 | Ph | C=O | H |
| 89 | H | D2 | A5 | A5 | Ph | C=O | H |
| 90 | H | D3 | A5 | A5 | Ph | C=O | H |
| 91 | D1 | D1 | A1 | A1 | Ph | C=O | H |
| 92 | D2 | D2 | A1 | A1 | Ph | C=O | H |
| 93 | D3 | D3 | A1 | A1 | Ph | C=O | H |
| 94 | D1 | D1 | A2 | A2 | Ph | C=O | H |
| 95 | D2 | D2 | A2 | A2 | Ph | C=O | H |
| 96 | D3 | D3 | A2 | A2 | Ph | C=O | H |
| 97 | D1 | D1 | A3 | A3 | Ph | C=O | H |
| 98 | D2 | D2 | A3 | A3 | Ph | C=O | H |
| 99 | D3 | D3 | A3 | A3 | Ph | C=O | H |
| 100 | D1 | D1 | A4 | A4 | Ph | C=O | H |
| 101 | D2 | D2 | A4 | A4 | Ph | C=O | H |
| 102 | D3 | D3 | A4 | A4 | Ph | C=O | H |
| 103 | D1 | D1 | A5 | A5 | Ph | C=O | H |
| 104 | D2 | D2 | A5 | A5 | Ph | C=O | H |
| 105 | D3 | D3 | A5 | A5 | Ph | C=O | H |

TABLE 4

| Compound No. | $R^3$ | $R^6$ | $R^{11}$ | $R^{14}$ | $R^{17}$ | Z | Other R |
|---|---|---|---|---|---|---|---|
| 106 | H | H | H | A1 | Ph | C=O | H |
| 107 | H | D1 | H | A1 | Ph | C=O | H |
| 108 | H | D2 | H | A1 | Ph | C=O | H |
| 109 | H | D3 | H | A1 | Ph | C=O | H |
| 110 | H | H | H | A2 | Ph | C=O | H |
| 111 | H | D1 | H | A2 | Ph | C=O | H |
| 112 | H | D2 | H | A2 | Ph | C=O | H |
| 113 | H | D3 | H | A2 | Ph | C=O | H |
| 114 | H | H | H | A3 | Ph | C=O | H |
| 115 | H | D1 | H | A3 | Ph | C=O | H |
| 116 | H | D2 | H | A3 | Ph | C=O | H |
| 117 | H | D3 | H | A3 | Ph | C=O | H |
| 118 | H | H | H | A4 | Ph | C=O | H |
| 119 | H | D1 | H | A4 | Ph | C=O | H |
| 120 | H | D2 | H | A4 | Ph | C=O | H |
| 121 | H | D3 | H | A4 | Ph | C=O | H |
| 122 | H | H | H | A5 | Ph | C=O | H |
| 123 | H | D1 | H | A5 | Ph | C=O | H |
| 124 | H | D2 | H | A5 | Ph | C=O | H |
| 125 | H | D3 | H | A5 | Ph | C=O | H |
| 126 | D1 | D1 | H | A1 | Ph | C=O | H |
| 127 | D2 | D2 | H | A1 | Ph | C=O | H |
| 128 | D3 | D3 | H | A1 | Ph | C=O | H |
| 129 | D1 | D1 | H | A2 | Ph | C=O | H |
| 130 | D2 | D2 | H | A2 | Ph | C=O | H |
| 131 | D3 | D3 | H | A2 | Ph | C=O | H |
| 132 | D1 | D1 | H | A3 | Ph | C=O | H |
| 133 | D2 | D2 | H | A3 | Ph | C=O | H |
| 134 | D3 | D3 | H | A3 | Ph | C=O | H |
| 135 | D1 | D1 | H | A4 | Ph | C=O | H |
| 136 | D2 | D2 | H | A4 | Ph | C=O | H |
| 137 | D3 | D3 | H | A4 | Ph | C=O | H |
| 138 | D1 | D1 | H | A5 | Ph | C=O | H |
| 139 | D2 | D2 | H | A5 | Ph | C=O | H |
| 140 | D3 | D3 | H | A5 | Ph | C=O | H |
| 141 | H | H | H | H | Ph | C=O | H |

TABLE 5

| Compound No. | R² | R⁷ | R¹⁰ | R¹⁵ | R¹⁷ | Z | Other R |
|---|---|---|---|---|---|---|---|
| 142 | H | H | A1 | A1 | Ph | C=S | H |
| 143 | H | D1 | A1 | A1 | Ph | C=S | H |
| 144 | H | D2 | A1 | A1 | Ph | C=S | H |
| 145 | H | D3 | A1 | A1 | Ph | C=S | H |
| 146 | H | H | A2 | A2 | Ph | C=S | H |
| 147 | H | D1 | A2 | A2 | Ph | C=S | H |
| 148 | H | D2 | A2 | A2 | Ph | C=S | H |
| 149 | H | D3 | A2 | A2 | Ph | C=S | H |
| 150 | H | H | A3 | A3 | Ph | C=S | H |
| 151 | H | D1 | A3 | A3 | Ph | C=S | H |
| 152 | H | D2 | A3 | A3 | Ph | C=S | H |
| 153 | H | D3 | A3 | A3 | Ph | C=S | H |
| 154 | H | H | A4 | A4 | Ph | C=S | H |
| 155 | H | D1 | A4 | A4 | Ph | C=S | H |
| 156 | H | D2 | A4 | A4 | Ph | C=S | H |
| 157 | H | D3 | A4 | A4 | Ph | C=S | H |
| 158 | H | H | A5 | A5 | Ph | C=S | H |
| 159 | H | D1 | A5 | A5 | Ph | C=S | H |
| 160 | H | D2 | A5 | A5 | Ph | C=S | H |
| 161 | H | D3 | A5 | A5 | Ph | C=S | H |
| 162 | D1 | D1 | A1 | A1 | Ph | C=S | H |
| 163 | D2 | D2 | A1 | A1 | Ph | C=S | H |
| 164 | D3 | D3 | A1 | A1 | Ph | C=S | H |
| 165 | D1 | D1 | A2 | A2 | Ph | C=S | H |
| 166 | D2 | D2 | A2 | A2 | Ph | C=S | H |
| 167 | D3 | D3 | A2 | A2 | Ph | C=S | H |
| 168 | D1 | D1 | A3 | A3 | Ph | C=S | H |
| 169 | D2 | D2 | A3 | A3 | Ph | C=S | H |
| 170 | D3 | D3 | A3 | A3 | Ph | C=S | H |
| 171 | D1 | D1 | A4 | A4 | Ph | C=S | H |
| 172 | D2 | D2 | A4 | A4 | Ph | C=S | H |
| 173 | D3 | D3 | A4 | A4 | Ph | C=S | H |
| 174 | D1 | D1 | A5 | A5 | Ph | C=S | H |
| 175 | D2 | D2 | A5 | A5 | Ph | C=S | H |
| 176 | D3 | D3 | A5 | A5 | Ph | C=S | H |

TABLE 6

| Compound No. | R³ | R⁶ | R¹¹ | R¹⁴ | R¹⁷ | Z | Other R |
|---|---|---|---|---|---|---|---|
| 177 | H | H | H | A1 | Ph | C=S | H |
| 178 | H | D1 | H | A1 | Ph | C=S | H |
| 179 | H | D2 | H | A1 | Ph | C=S | H |
| 180 | H | D3 | H | A1 | Ph | C=S | H |
| 181 | H | H | H | A2 | Ph | C=S | H |
| 182 | H | D1 | H | A2 | Ph | C=S | H |
| 183 | H | D2 | H | A2 | Ph | C=S | H |
| 184 | H | D3 | H | A2 | Ph | C=S | H |
| 185 | H | H | H | A3 | Ph | C=S | H |
| 186 | H | D1 | H | A3 | Ph | C=S | H |
| 187 | H | D2 | H | A3 | Ph | C=S | H |
| 188 | H | D3 | H | A3 | Ph | C=S | H |
| 189 | H | H | H | A4 | Ph | C=S | H |
| 190 | H | D1 | H | A4 | Ph | C=S | H |
| 191 | H | D2 | H | A4 | Ph | C=S | H |
| 192 | H | D3 | H | A4 | Ph | C=S | H |
| 193 | H | H | H | A5 | Ph | C=S | H |
| 194 | H | D1 | H | A5 | Ph | C=S | H |
| 195 | H | D2 | H | A5 | Ph | C=S | H |
| 196 | H | D3 | H | A5 | Ph | C=S | H |
| 197 | D1 | D1 | H | A1 | Ph | C=S | H |
| 198 | D2 | D2 | H | A1 | Ph | C=S | H |
| 199 | D3 | D3 | H | A1 | Ph | C=S | H |
| 200 | D1 | D1 | H | A2 | Ph | C=S | H |
| 201 | D2 | D2 | H | A2 | Ph | C=S | H |
| 202 | D3 | D3 | H | A2 | Ph | C=S | H |
| 203 | D1 | D1 | H | A3 | Ph | C=S | H |
| 204 | D2 | D2 | H | A3 | Ph | C=S | H |
| 205 | D3 | D3 | H | A3 | Ph | C=S | H |
| 206 | D1 | D1 | H | A4 | Ph | C=S | H |
| 207 | D2 | D2 | H | A4 | Ph | C=S | H |
| 208 | D3 | D3 | H | A4 | Ph | C=S | H |
| 209 | D1 | D1 | H | A5 | Ph | C=S | H |
| 210 | D2 | D2 | H | A5 | Ph | C=S | H |
| 211 | D3 | D3 | H | A5 | Ph | C=S | H |
| 212 | H | H | H | H | Ph | C=S | H |

TABLE 7

| Compound No. | R² | R⁷ | R¹⁰ | R¹⁵ | R¹⁷ | Z | Other R |
|---|---|---|---|---|---|---|---|
| 213 | H | H | A1 | A1 | Ph | C=C(CN)₂ | H |
| 214 | H | D1 | A1 | A1 | Ph | C=C(CN)₂ | H |
| 215 | H | D2 | A1 | A1 | Ph | C=C(CN)₂ | H |
| 216 | H | D3 | A1 | A1 | Ph | C=C(CN)₂ | H |
| 217 | H | H | A2 | A2 | Ph | C=C(CN)₂ | H |
| 218 | H | D1 | A2 | A2 | Ph | C=C(CN)₂ | H |
| 219 | H | D2 | A2 | A2 | Ph | C=C(CN)₂ | H |
| 220 | H | D3 | A2 | A2 | Ph | C=C(CN)₂ | H |
| 221 | H | H | A3 | A3 | Ph | C=C(CN)₂ | H |
| 222 | H | D1 | A3 | A3 | Ph | C=C(CN)₂ | H |
| 223 | H | D2 | A3 | A3 | Ph | C=C(CN)₂ | H |
| 224 | H | D3 | A3 | A3 | Ph | C=C(CN)₂ | H |
| 225 | H | H | A4 | A4 | Ph | C=C(CN)₂ | H |
| 226 | H | D1 | A4 | A4 | Ph | C=C(CN)₂ | H |
| 227 | H | D2 | A4 | A4 | Ph | C=C(CN)₂ | H |
| 228 | H | D3 | A4 | A4 | Ph | C=C(CN)₂ | H |
| 229 | H | H | A5 | A5 | Ph | C=C(CN)₂ | H |
| 230 | H | D1 | A5 | A5 | Ph | C=C(CN)₂ | H |
| 231 | H | D2 | A5 | A5 | Ph | C=C(CN)₂ | H |
| 232 | H | D3 | A5 | A5 | Ph | C=C(CN)₂ | H |
| 233 | D1 | D1 | A1 | A1 | Ph | C=C(CN)₂ | H |
| 234 | D2 | D2 | A1 | A1 | Ph | C=C(CN)₂ | H |
| 235 | D3 | D3 | A1 | A1 | Ph | C=C(CN)₂ | H |
| 236 | D1 | D1 | A2 | A2 | Ph | C=C(CN)₂ | H |
| 237 | D2 | D2 | A2 | A2 | Ph | C=C(CN)₂ | H |
| 238 | D3 | D3 | A2 | A2 | Ph | C=C(CN)₂ | H |
| 239 | D1 | D1 | A3 | A3 | Ph | C=C(CN)₂ | H |
| 240 | D2 | D2 | A3 | A3 | Ph | C=C(CN)₂ | H |
| 241 | D3 | D3 | A3 | A3 | Ph | C=C(CN)₂ | H |
| 242 | D1 | D1 | A4 | A4 | Ph | C=C(CN)₂ | H |
| 243 | D2 | D2 | A4 | A4 | Ph | C=C(CN)₂ | H |
| 244 | D3 | D3 | A4 | A4 | Ph | C=C(CN)₂ | H |
| 245 | D1 | D1 | A5 | A5 | Ph | C=C(CN)₂ | H |
| 246 | D2 | D2 | A5 | A5 | Ph | C=C(CN)₂ | H |
| 247 | D3 | D3 | A5 | A5 | Ph | C=C(CN)₂ | H |

TABLE 8

| Compound No. | R³ | R⁶ | R¹¹ | R¹⁴ | R¹⁷ | Z | Other R |
|---|---|---|---|---|---|---|---|
| 248 | H | H | H | A1 | Ph | C=C(CN)₂ | H |
| 249 | H | D1 | H | A1 | Ph | C=C(CN)₂ | H |
| 250 | H | D2 | H | A1 | Ph | C=C(CN)₂ | H |
| 251 | H | D3 | H | A1 | Ph | C=C(CN)₂ | H |
| 252 | H | H | H | A2 | Ph | C=C(CN)₂ | H |
| 253 | H | D1 | H | A2 | Ph | C=C(CN)₂ | H |
| 254 | H | D2 | H | A2 | Ph | C=C(CN)₂ | H |
| 255 | H | D3 | H | A2 | Ph | C=C(CN)₂ | H |
| 256 | H | H | H | A3 | Ph | C=C(CN)₂ | H |
| 257 | H | D1 | H | A3 | Ph | C=C(CN)₂ | H |
| 258 | H | D2 | H | A3 | Ph | C=C(CN)₂ | H |
| 259 | H | D3 | H | A3 | Ph | C=C(CN)₂ | H |
| 260 | H | H | H | A4 | Ph | C=C(CN)₂ | H |
| 261 | H | D1 | H | A4 | Ph | C=C(CN)₂ | H |
| 262 | H | D2 | H | A4 | Ph | C=C(CN)₂ | H |
| 263 | H | D3 | H | A4 | Ph | C=C(CN)₂ | H |
| 264 | H | H | H | A5 | Ph | C=C(CN)₂ | H |
| 265 | H | D1 | H | A5 | Ph | C=C(CN)₂ | H |
| 266 | H | D2 | H | A5 | Ph | C=C(CN)₂ | H |
| 267 | H | D3 | H | A5 | Ph | C=C(CN)₂ | H |
| 268 | D1 | D1 | H | A1 | Ph | C=C(CN)₂ | H |
| 269 | D2 | D2 | H | A1 | Ph | C=C(CN)₂ | H |

TABLE 8-continued

| Compound No. | $R^3$ | $R^6$ | $R^{11}$ | $R^{14}$ | $R^{17}$ | Z | Other R |
|---|---|---|---|---|---|---|---|
| 270 | D3 | D3 | H | A1 | Ph | C=C(CN)$_2$ | H |
| 271 | D1 | D1 | H | A2 | Ph | C=C(CN)$_2$ | H |
| 272 | D2 | D2 | H | A2 | Ph | C=C(CN)$_2$ | H |
| 273 | D3 | D3 | H | A2 | Ph | C=C(CN)$_2$ | H |
| 274 | D1 | D1 | H | A3 | Ph | C=C(CN)$_2$ | H |
| 275 | D2 | D2 | H | A3 | Ph | C=C(CN)$_2$ | H |
| 276 | D3 | D3 | H | A3 | Ph | C=C(CN)$_2$ | H |
| 277 | D1 | D1 | H | A4 | Ph | C=C(CN)$_2$ | H |
| 278 | D2 | D2 | H | A4 | Ph | C=C(CN)$_2$ | H |
| 279 | D3 | D3 | H | A4 | Ph | C=C(CN)$_2$ | H |
| 280 | D1 | D1 | H | A5 | Ph | C=C(CN)$_2$ | H |
| 281 | D2 | D2 | H | A5 | Ph | C=C(CN)$_2$ | H |
| 282 | D3 | D3 | H | A5 | Ph | C=C(CN)$_2$ | H |
| 283 | H | H | H | H | Ph | C=C(CN)$_2$ | H |

TABLE 9

| Compound No. | $R^2$ | $R^7$ | $R^{10}$ | $R^{15}$ | $R^{17}$ | Z | Other R |
|---|---|---|---|---|---|---|---|
| 284 | H | H | A1 | A1 | Ph | C=C(COOH)$_2$ | H |
| 285 | H | D1 | A1 | A1 | Ph | C=C(COOH)$_2$ | H |
| 286 | H | D2 | A1 | A1 | Ph | C=C(COOH)$_2$ | H |
| 287 | H | D3 | A1 | A1 | Ph | C=C(COOH)$_2$ | H |
| 288 | H | H | A2 | A2 | Ph | C=C(COOH)$_2$ | H |
| 289 | H | D1 | A2 | A2 | Ph | C=C(COOH)$_2$ | H |
| 290 | H | D2 | A2 | A2 | Ph | C=C(COOH)$_2$ | H |
| 291 | H | D3 | A2 | A2 | Ph | C=C(COOH)$_2$ | H |
| 292 | H | H | A3 | A3 | Ph | C=C(COOH)$_2$ | H |
| 293 | H | D1 | A3 | A3 | Ph | C=C(COOH)$_2$ | H |
| 294 | H | D2 | A3 | A3 | Ph | C=C(COOH)$_2$ | H |
| 295 | H | D3 | A3 | A3 | Ph | C=C(COOH)$_2$ | H |
| 296 | H | H | A4 | A4 | Ph | C=C(COOH)$_2$ | H |
| 297 | H | D1 | A4 | A4 | Ph | C=C(COOH)$_2$ | H |
| 298 | H | D2 | A4 | A4 | Ph | C=C(COOH)$_2$ | H |
| 299 | H | D3 | A4 | A4 | Ph | C=C(COOH)$_2$ | H |
| 300 | H | H | A5 | A5 | Ph | C=C(COOH)$_2$ | H |
| 301 | H | D1 | A5 | A5 | Ph | C=C(COOH)$_2$ | H |
| 302 | H | D2 | A5 | A5 | Ph | C=C(COOH)$_2$ | H |
| 303 | H | D3 | A5 | A5 | Ph | C=C(COOH)$_2$ | H |
| 304 | D1 | D1 | A1 | A1 | Ph | C=C(COOH)$_2$ | H |
| 305 | D2 | D2 | A1 | A1 | Ph | C=C(COOH)$_2$ | H |
| 306 | D3 | D3 | A1 | A1 | Ph | C=C(COOH)$_2$ | H |
| 307 | D1 | D1 | A2 | A2 | Ph | C=C(COOH)$_2$ | H |
| 308 | D2 | D2 | A2 | A2 | Ph | C=C(COOH)$_2$ | H |
| 309 | D3 | D3 | A2 | A2 | Ph | C=C(COOH)$_2$ | H |
| 310 | D1 | D1 | A3 | A3 | Ph | C=C(COOH)$_2$ | H |
| 311 | D2 | D2 | A3 | A3 | Ph | C=C(COOH)$_2$ | H |
| 312 | D3 | D3 | A3 | A3 | Ph | C=C(COOH)$_2$ | H |
| 313 | D1 | D1 | A4 | A4 | Ph | C=C(COOH)$_2$ | H |
| 314 | D2 | D2 | A4 | A4 | Ph | C=C(COOH)$_2$ | H |
| 315 | D3 | D3 | A4 | A4 | Ph | C=C(COOH)$_2$ | H |
| 316 | D1 | D1 | A5 | A5 | Ph | C=C(COOH)$_2$ | H |
| 317 | D2 | D2 | A5 | A5 | Ph | C=C(COOH)$_2$ | H |
| 318 | D3 | D3 | A5 | A5 | Ph | C=C(COOH)$_2$ | H |

TABLE 10

| Compound No. | $R^3$ | $R^6$ | $R^{11}$ | $R^{14}$ | $R^{17}$ | Z | Other R |
|---|---|---|---|---|---|---|---|
| 319 | H | H | H | A1 | Ph | C=C(COOH)$_2$ | H |
| 320 | H | D1 | H | A1 | Ph | C=C(COOH)$_2$ | H |
| 321 | H | D2 | H | A1 | Ph | C=C(COOH)$_2$ | H |
| 322 | H | D3 | H | A1 | Ph | C=C(COOH)$_2$ | H |
| 323 | H | H | H | A2 | Ph | C=C(COOH)$_2$ | H |
| 324 | H | D1 | H | A2 | Ph | C=C(COOH)$_2$ | H |
| 325 | H | D2 | H | A2 | Ph | C=C(COOH)$_2$ | H |
| 326 | H | D3 | H | A2 | Ph | C=C(COOH)$_2$ | H |
| 327 | H | H | H | A3 | Ph | C=C(COOH)$_2$ | H |
| 328 | H | D1 | H | A3 | Ph | C=C(COOH)$_2$ | H |
| 329 | H | D2 | H | A3 | Ph | C=C(COOH)$_2$ | H |

TABLE 10-continued

| Compound No. | $R^3$ | $R^6$ | $R^{11}$ | $R^{14}$ | $R^{17}$ | Z | Other R |
|---|---|---|---|---|---|---|---|
| 330 | H | D3 | H | A3 | Ph | C=C(COOH)$_2$ | H |
| 331 | H | H | H | A4 | Ph | C=C(COOH)$_2$ | H |
| 332 | H | D1 | H | A4 | Ph | C=C(COOH)$_2$ | H |
| 333 | H | D2 | H | A4 | Ph | C=C(COOH)$_2$ | H |
| 334 | H | D3 | H | A4 | Ph | C=C(COOH)$_2$ | H |
| 335 | H | H | H | A5 | Ph | C=C(COOH)$_2$ | H |
| 336 | H | D1 | H | A5 | Ph | C=C(COOH)$_2$ | H |
| 337 | H | D2 | H | A5 | Ph | C=C(COOH)$_2$ | H |
| 338 | H | D3 | H | A5 | Ph | C=C(COOH)$_2$ | H |
| 339 | D1 | D1 | H | A1 | Ph | C=C(COOH)$_2$ | H |
| 340 | D2 | D2 | H | A1 | Ph | C=C(COOH)$_2$ | H |
| 341 | D3 | D3 | H | A1 | Ph | C=C(COOH)$_2$ | H |
| 342 | D1 | D1 | H | A2 | Ph | C=C(COOH)$_2$ | H |
| 343 | D2 | D2 | H | A2 | Ph | C=C(COOH)$_2$ | H |
| 344 | D3 | D3 | H | A2 | Ph | C=C(COOH)$_2$ | H |
| 345 | D1 | D1 | H | A3 | Ph | C=C(COOH)$_2$ | H |
| 346 | D2 | D2 | H | A3 | Ph | C=C(COOH)$_2$ | H |
| 347 | D3 | D3 | H | A3 | Ph | C=C(COOH)$_2$ | H |
| 348 | D1 | D1 | H | A4 | Ph | C=C(COOH)$_2$ | H |
| 349 | D2 | D2 | H | A4 | Ph | C=C(COOH)$_2$ | H |
| 350 | D3 | D3 | H | A4 | Ph | C=C(COOH)$_2$ | H |
| 351 | D1 | D1 | H | A5 | Ph | C=C(COOH)$_2$ | H |
| 352 | D2 | D2 | H | A5 | Ph | C=C(COOH)$_2$ | H |
| 353 | D3 | D3 | H | A5 | Ph | C=C(COOH)$_2$ | H |
| 354 | H | H | H | H | Ph | C=C(COOH)$_2$ | H |

[Production Method for Compounds Represented by General Formula (1)]

The production method for the compounds represented by the general formula (1) is not specifically defined. The compounds represented by the general formula (1) may be produced by suitably combining known production methods and conditions.

For example, one preferred production method is represented by the scheme mentioned below. Here as one typical example, a production method for a compound represented by a general formula (15) is described, in which the acridine structure is substituted with one electron-donating group D, the nitrogen atom of the acridine structure is substituted with $R^{17}$, and the fluorene structure is substituted with one electron-withdrawing group A.

[Chem. 20]

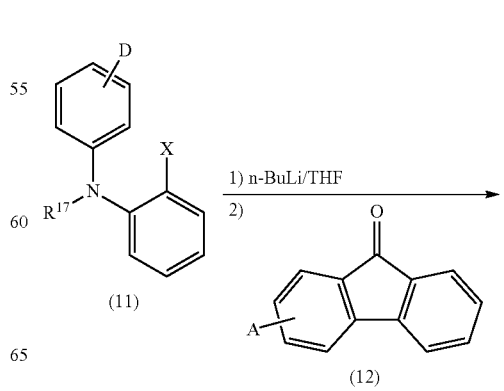

-continued

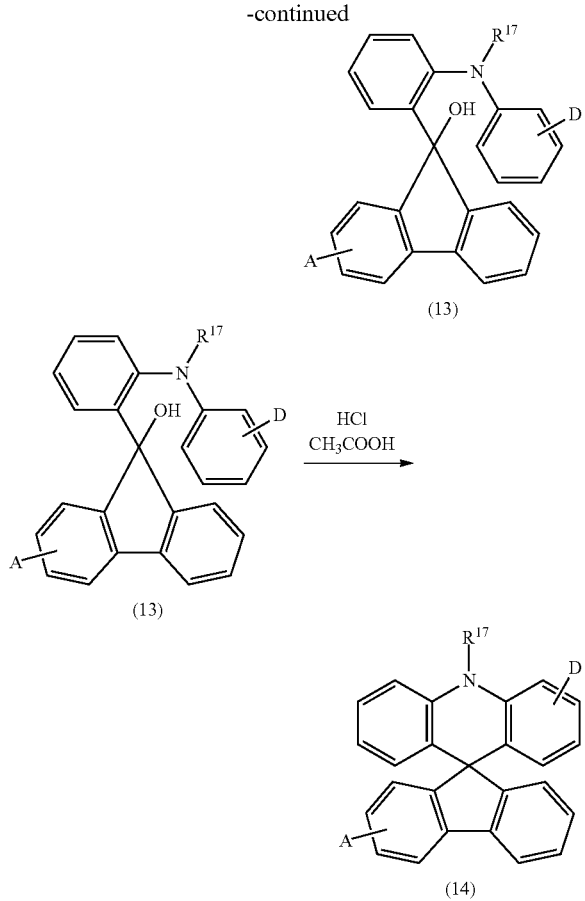

In the above scheme, first the halogen-substituted diphenylamine represented by the general formula (11) is reacted with n-butyllithium, and then further reacted with the fluorene represented by the general formula (12). Acetic acid and concentrated hydrochloric acid are added to the fluorene derivative obtained through the previous reaction and represented by the general formula (13), and heated for cyclization to give the intended product represented by the general formula (14). X in the general formula (11) represents a halogen atom. Concretely, X includes a fluorine atom, a chlorine atom, a bromine atom and an iodine atom, and is preferably a chlorine atom, a bromine atom or an iodine atom, more preferably a bromine atom. In the general formulae (11), (13) and (14), D represents an electron-donating group; and in the general formulae (12), (13) and (14), A represents an electron-withdrawing group. In the coupling reaction of the first step and the cyclization of the second step, employable are reaction conditions generally used in the same type of the coupling reaction and the cyclization.

Regarding the production methods for the compounds represented by the general formula (1) except the general formula (14), those compounds may be produced in accordance with the method of the above scheme. For example, of the compounds represented by the general formula (1), those having an anthrone structure may be produced in the same manner as above but using an anthraquinone (anthracene-9,10-quinone) substituted with the electron-withdrawing group A in place of the compound represented by the general formula (12) in the above scheme. Depending on the type of the electron-donating group D and the type of the electron-withdrawing group A to be introduced into the spiro ring, reaction specific to the substituents may be utilized here. For example, in case where a cyano group is introduced as the electron-withdrawing group, a spiro compound substituted with a halogen atom at the position at which the cyano group is to be introduced is first prepared, and then the compound is reacted with CuCN at the halogen atom whereby the halogen atom may be converted into the cyano group.

For the details of the reaction, referred to are Synthesis Examples to be given hereinunder. The compounds represented by the general formula (1) may also be produced by combining any other known reactions.

[Organic Electroluminescence Element]

The organic electroluminescence element of the invention is provided with a configuration having an anode, a cathode and an organic layer between the anode and the cathode. The organic layer contains at least a light-emitting layer, and may be a light-emitting layer alone or may have any one or more organic layers in addition to a light-emitting layer. The organic electroluminescence element of the invention contains the compound represented by the general formula (1) in the light-emitting layer therein.

When the compound represented by the general formula (1) is used in the light-emitting layer of an organic electroluminescence element as a thermally-activated delayed fluorescence material, then the element secures a high emission efficiency more inexpensively than before. Heretofore, for producing an organic electroluminescence element having a high emission efficiency, there have been actively made studies using a phosphorescence material having a high exciton production efficiency. However, using a phosphorescence material has a problem in that the cost is high as requiring use of a rare metal such as Ir or Pt. Using a delayed fluorescence material does not require such an expensive material, therefore making it possible to inexpensively provide an organic electroluminescence element having a high emission efficiency.

The organic electroluminescence element of the invention has a laminate configuration of at least an anode, an organic layer and a cathode. A single-layer organic electroluminescence element may comprise a light-emitting layer alone between the anode and the cathode; however, it is desirable that the organic electroluminescence element of the invention is provided with multiple organic layers. The other organic layers than the light-emitting layer may be referred to as a hole injection layer, a hole transport layer, an electron blocking layer, a light-emitting layer, a hole blocking layer, an electron transport layer, an electron injection layer or the like, depending on the functions thereof, for which any known material may be used as suitably combined. As specific configuration examples including an anode and a cathode, there may be mentioned anode/light-emitting layer/cathode, anode/hole injection layer/light-emitting layer/cathode, anode/hole injection layer/hole transport layer/light-emitting layer/cathode, anode/hole injection layer/light-emitting layer/electron injection layer/cathode, anode/hole injection layer/hole transport layer/light-emitting layer/electron injection layer/cathode, anode/hole injection layer/light-emitting layer/electron transport layer/electron injection layer/cathode, anode/hole injection layer/hole transport layer/light-emitting layer/electron transport layer/electron injection layer/cathode, anode/light-emitting layer/electron injection layer/cathode, anode/light-emitting layer/electron injection layer/electron transport layer/cathode, anode/hole injection layer/light-emitting layer/hole blocking layer/electron injection layer/cathode. The configuration of anode/organic layer/cathode may be formed on a substrate. The configurations that may be employed in the invention should not be limited to those exemplifications. Especially preferably, the compound represented by the general formula (1) is used in the light-emitting layer, which, however, does not exclude use of the compound represented by the general formula (1) in the other organic layer than the light-emitting layer as a charge transport material or the like therein.

In producing the organic layers and the electrodes that constitute the organic electroluminescence element of the invention, any known production methods may be employed as suitably selected. In addition, various materials generally employed in known organic electroluminescence elements can be selected and used in those organic layers and electrodes. Further, various modifications of known techniques and those that may be readily anticipated from known techniques may be optionally applied to the organic electroluminescence element of the invention. Typical materials of constituting the organic electroluminescence element of the invention are described below; however, the materials usable for the organic electroluminescence element of the invention should not be limitatively interpreted by the following description.

(Substrate)

The substrate functions as a support of supporting the configuration of anode/organic layer/cathode and further functions as a substrate in producing the configuration of anode/organic layer/cathode. The substrate may be formed of a transparent material, or may also be formed of a semitransparent or nontransparent material. In case where emitted light is taken out from the side of the anode, a transparent substrate is preferably used. The material to constitute the substrate includes glass, quartz, metal, polycarbonate, polyester, polymethacrylate, polysulfone. When a flexible substrate is sued, then there may be provided a flexible organic electroluminescence element.

(Anode)

The anode has a function of injecting holes toward the organic layer. As the anode, preferably used is a material having a high work function. For example, a material having a work function of at least 4 eV is preferably used. Concretely, there are mentioned metals (for example, aluminium, gold, silver, nickel, palladium, platinum), metal oxides (for example, indium oxide, tin oxide, zinc oxide, mixture of indium oxide and tin oxide [ITO], mixture of zinc oxide and indium oxide [IZO]), metal halides (for example, copper iodide), carbon black. In addition, also employable are electroconductive polymers such as polyaniline, poly(3-methylthiophene), polypyrrole, etc. In case where emitted light is taken out from the side of the anode, preferred is use of a material having a high light transmittance for the emitted light, such as ITO, IZO or the like. The transmittance is preferably at least 10%, more preferably at least 50%, even more preferably at least 80%. The thickness of the anode is generally at least 3 nm, but preferably at least 10 nm. The upper limit may be, for example, at most 1 μm, however, when the anode is not required to have transparency, the thickness thereof may be further larger, and for example, such a thick anode may additionally serve also as the above-mentioned substrate. The anode may be formed, for example, according to a vapor deposition method, a sputtering method, or a coating method. In case where an electroconductive polymer is used for the anode, the anode may be formed on the substrate according to an electrolytic polymerization method. After the anode formation, the surface may be processed for the purpose of improving the hole injection function thereof. Specific examples of the surface treatment include plasma treatment (for example, argon plasma treatment, oxygen plasma treatment), UV treatment, ozone treatment, etc.

(Hole Injection Layer and Hole Transport Layer)

The hole injection layer has a function of transporting holes from the anode to the side of the light-emitting layer. The hole injection layer is formed generally on the anode, and therefore the layer is preferably excellent in the adhesiveness to the anode surface. Consequently, it is desirable that the layer is formed of a material having good thin-film formability. The hole transport layer has a function of transporting holes to the side of the light-emitting layer. The hole transport layer is formed of a material having excellent hole transportability.

For the hole injection layer and the hole transport layer, used are hole transport materials having a high hole mobility and a small ionization energy. The ionization energy of the material is, for example, preferably from 4.5 to 6.0 eV. As the hole transport material, various materials that are said to be usable as the hole injection layer or the hole transport layer of organic electroluminescence elements may be used here as suitably selected. The hole transport material may be a polymer material having a recurring unit or may also be a low-molecular compound.

As the hole transport material, for example, there may be mentioned aromatic tertiary amine compounds, styrylamine compounds, oxadiazole derivatives, imidazole derivatives, triazole derivatives, pyrazoline derivatives, pyrazolone derivatives, phenylenediamine derivatives, arylamine derivatives, amino-substituted chalcone derivatives, oxazole derivatives, polyarylalkane derivatives, styrylanthracene derivatives, fluorenone derivatives, hydrazone derivatives, stilbene derivatives, silazane derivatives, silane polymers, aniline copolymers, thiophene polymers, porphyrin compounds.

As a preferred hole transport material, there are mentioned aromatic tertiary amine compounds, concretely including triphenylamine, tritolylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cyclohexane, N,N'-bis(4'-diphenylamino-4-biphenylyl)-N,N'-diphenylbenzidine, N,N'-bis(4'-diphenylamino-4-phenyl)-N,N'-diphenylbenzidine, N,N'-bis(4'-diphenylamino-4-phenyl)-N,N'-di(1-naphthyl)benzidine, N,N'-bis(4'-phenyl(1-naphthyl)amino-4-phenyl)-N,N'-diphenyl benzidine, N,N'-bis(4'-phenyl(1-naphthyl)amino-4-phenyl)-N,N'-di(1-naphthyl)benzidine, etc. Also as a preferred hole transport material, phthalocyanine compounds are mentioned. Concretely, there are mentioned H$_2$Pc, CuPc, CoPc, NiPc, ZnPc, PdPc, FePc, MnPc, ClAlPc, ClGaPc, ClInPc, ClSnPc, Cl$_2$SiPc, (HO)AlPc, (HO)GaPc, VOPc, TiOPc, MoOPc, GaPc—O—GaPc [Pc means phthalocyanine]. Further, also preferred is use of poly(ethylenedioxy)thiophene (PEDOT), metal oxides such as molybdenum oxide and the like, and known aniline derivatives.

One alone or two or more different types of hole transport materials may be used in one layer, either singly or as combined therein. The hole injection layer and the hole transport layer may be formed, for example, according to a vapor deposition method, a sputtering method or a coating method. The thickness of the hole injection layer and the hole transport layer may be generally at least 3 nm each but preferably at least 10 nm each. The upper limit may be, for example, at most 5 μm each.

(Light-Emitting Layer)

The light-emitting layer in the organic electroluminescence element of the invention may contain a host material and a dopant material, or may be formed of a single material. The light-emitting layer in the organic electroluminescence element of the invention contains the compound represented by the general formula (1).

When the light-emitting layer contains a host material and a dopant material, preferably, the amount of the dopant material is at most 10% by weight of the host material therein for the purpose of preventing concentration quenching, more preferably at most 6% by weight. One material alone or two or more different types of materials may be used either singly or as combined for the dopant material and the host material. The doping may be attained by co-deposition of the host material and the dopant material, in which the host material and the dopant material may be previously mixed for simultaneous vapor deposition.

As the host material for use in the light-emitting layer, there are mentioned carbazole derivatives, quinolinol derivative metal complexes, oxadiazole derivatives, distyrylarylene derivatives, diphenylanthracene derivatives, etc. In addition to these, also usable here are those that are proposed as the host material in a light-emitting layer, as suitably selected. As a preferred host material, for example, there are mentioned the compounds represented by the following general formula (10):

[Chem. 21]

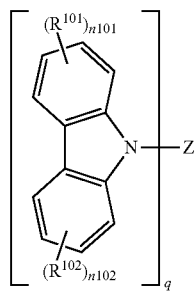

General Formula (10)

In the general formula (10), Z represents a q-valent linking group; and q indicates an integer of from 2 to 4. $R^{101}$ and $R^{102}$ each independently represent a substituent; and n101 and n102 each independently indicate an integer of from 0 to 4. When n101 is an integer of from 2 to 4, n101's $R^{101}$'s may be the same or different; and when n102 is an integer of from 2 to 4, n102's $R^{102}$'s may be the same or different. Further, $R^{101}$, $R^{102}$, n101 and n102 in q's constitutive elements may be the same or different.

As the substituent represented by $R^{101}$ and $R^{102}$ in the general formula (10) includes, for example, a substituted or unsubstituted alkyl group, a substituted or unsubstituted alkoxy group, a substituted or unsubstituted aryl group, a substituted or unsubstituted aryloxy group, a substituted or unsubstituted alkenyl group, a substituted or unsubstituted amino group, a halogen atom, a cyano group. Preferred are a substituted or unsubstituted alkyl group, a substituted or unsubstituted aryl group, a substituted or unsubstituted alkoxy group, a substituted or unsubstituted aryloxy group; and more preferred are a substituted or unsubstituted alkyl group, a substituted or unsubstituted aryl group.

Preferably, n101 and n102 each are independently an integer of from 0 to 3, more preferably an integer of from 0 to 2. Also preferably, both n101 and n102 are 0.

Z in the general formula (10) is preferably a linking group that contains an aromatic ring or a hetero ring. The aromatic ring may be a single ring or a fused ring of two or more aromatic rings fused together. The carbon number of the aromatic ring is preferably from 6 to 22, more preferably from 6 to 18, even more preferably from 6 to 14, still more preferably from 6 to 10. Specific examples of the aromatic ring include a benzene ring and a naphthalene ring. The hetero ring may be a single ring, or a fused ring of one or more hetero ring fused with an aromatic ring or a hetero ring. The carbon number of the hetero ring is preferably from 5 to 22, more preferably from to 18, even more preferably from 5 to 14, still more preferably from 5 to 10. Preferably, the hetero atom to constitute the hetero ring is a nitrogen atom. Specific examples of the hetero ring include a pyridine ring, a pyridazine ring, a pyrimidine ring, a triazine ring, a triazole ring, a benzotriazole ring. Z in the general formula (10) may contain an aromatic ring or a hetero ring and may additionally contain a nonaromatic linking group. The nonaromatic linking group includes the following structures:

[Chem. 22]

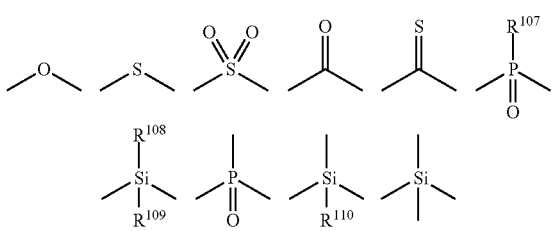

$R^{107}$, $R^{108}$, $R^{109}$ and $R^{110}$ in the above nonaromatic linking group each independently represent a hydrogen atom, a substituted or unsubstituted alkyl group or a substituted or unsubstituted aryl group, but preferably a substituted or unsubstituted alkyl group or a substituted or unsubstituted aryl group.

As preferred host materials, for example, there are mentioned compounds represented by the following general formula (11):

[Chem. 23]

General Formula (11)

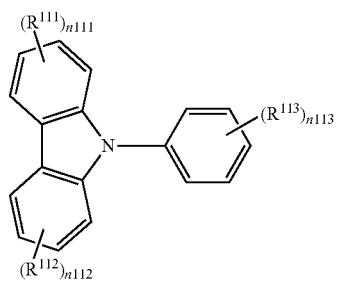

In the general formula (11), $R^{111}$, $R^{112}$ and $R^{113}$ each independently represent a substituent, n111 and n112 each independently indicate an integer of from 1 to 4, n113 indicates an integer of from 1 to 5. At least one $R^{111}$, at least one $R^{112}$, and at least one $R^{113}$ each are an aryl group. When n111 is an integer of from 2 to 4, n111's $R^{111}$'s may be the same or different; when n112 is an integer of from 2 to 4, n112's $R^{112}$'s may be the same or different; and when n113 is an integer of from 2 to 5, n113's $R^{113}$'s may be the same or different.

Preferably, in the general formula (11), n111, n112 and n113 each are from 1 to 3, more preferably 1 or 2.

In the following, specific examples of the compounds represented by the general formula (10) or the general formula (11) are shown; however, the compounds represented by the general formula (10) or the general formula (11) for use in the invention should not be limitatively interpreted by these specific examples.

[Chem. 24]

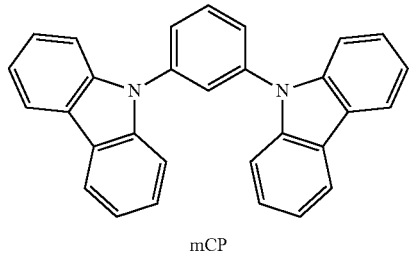

mCP

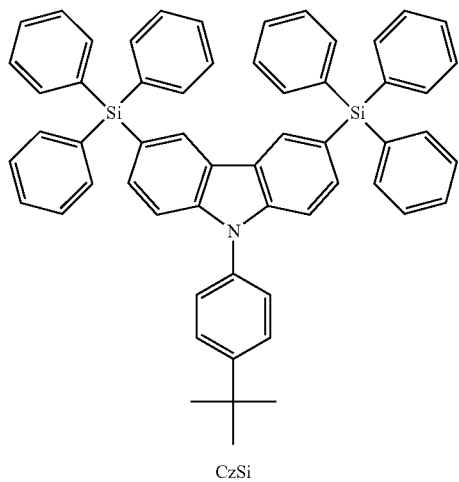

CzSi

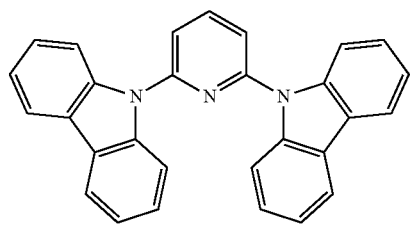

PYD2

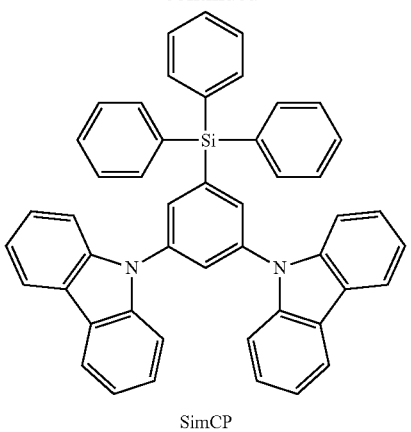

SimCP

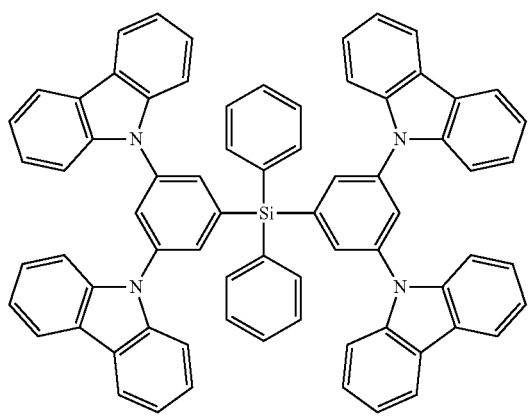

SimCP2

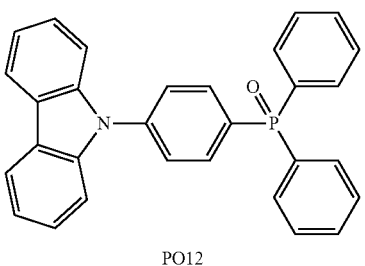

PO12

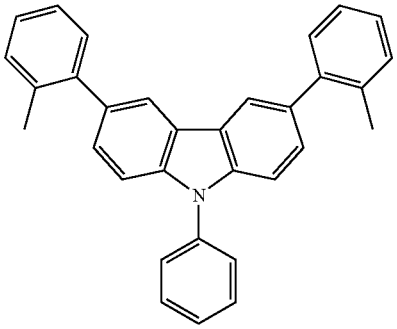

CBZ

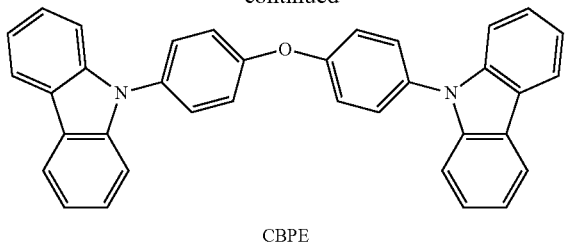

CBPE (Hole Blocking Layer)

The hole blocking layer has a function of preventing the holes having passed through the light-emitting layer from moving toward the side of cathode. Preferably, the hole blocking layer is formed between the light-emitting layer and the organic layer on the cathode side. The organic material to form the hole blocking layer includes aluminium complex compounds, gallium complex compounds, phenanthroline derivatives, silol derivatives, quinolinol derivative metal complexes, oxadiazole derivatives, oxazole derivatives. Concretely, there are mentioned bis(8-hydroxyquinolinate)(4-phenylphenolate)aluminium, bis(2-methyl-8-hydroxyquinolinate)(4-phenylphenolate)gallium, 2,9-dimethyl-4,7-diphenyl-1,10-phenanthroline (BCP), etc. One organic material alone or two or more different types of organic materials may be selected for the hole blocking layer either singly or as combined. The hole blocking layer may be formed, for example, according to a vapor deposition method, a sputtering method or a coating method. The thickness of the hole blocking layer may be generally at least 3 nm but is preferably at least 10 nm. The upper limit may be, for example, at most 5 μm.

(Electron Injection Layer and Electron Transport Layer)

The electron injection layer has a function of transporting electrons from the cathode to the side of the light-emitting layer. The electron injection layer is formed generally so as to be in contact with the cathode, and therefore the layer is preferably excellent in the adhesiveness to the cathode surface. The electron transport layer has a function of transporting electrons to the side of the light-emitting layer. The electron transport layer is formed of a material excellent in electron transportability.

For the electron injection layer and the electron transport layer, used are electron transport materials having a high electron mobility and a large ionization energy. As the electron transport material, various materials that are said to be usable as the electron injection layer or the electron transport layer of organic electroluminescence elements may be used here as suitably selected. The electron transport material may be a polymer material having a recurring unit or may also be a low-molecular compound.

As the electron transport material, for example, there may be mentioned fluorenone derivatives, anthraquinodimethane derivatives, diphenoquinone derivatives, thiopyran dioxide derivatives, oxazole derivatives, thiazole derivatives, oxadiazole derivatives, triazole derivatives, imidazole derivatives, perylenetetracarboxylic acid derivatives, quinoxaline derivatives, fluorenylidenemethane derivatives, anthraquinodimethane derivatives, anthrone derivatives, etc. Specific examples of preferred electron transport materials include 2,5-bis(1-phenyl)-1,3,4-oxazole, 2,5-bis(1-phenyl)-1,3,4-thiazole, 2,5-bis(1-phenyl)-1,3,4-oxadiazole, 2-(4'-tert-butylphenyl)-5-(4''-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4''-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4''-biphenyl)-1,3,4-triazole, 2,5-bis(1-naphthyl)-1,3,4-triazole, 1,4-bis[2-(5-phenyltriazolyl)]benzene, lithium 8-hydroxyquinolinate, zinc bis(8-hydroxyquinolinate), copper bis(8-hydroxyquinolinate), manganese bis(8-hydroxyquinolinate), aluminium tris(8-hydroxyquinolinate), aluminium tris(2-methyl-8-hydroxyquinolinate), gallium tris(8-hydroxyquinolinate), beryllium bis(10-hydroxybenzo[h]quinolinate), zinc bis(10-hydroxybenzo[h]quinolinate), chlorogallium bis(2-methyl-8-quinolinate), gallium bis(2-methyl-8-quinolinate)(o-cresolate), aluminium bis(2-methyl-8-quinolinate)(1-naphtholate), gallium bis(2-methyl-8-quinolinate)(2-naphtholate), etc.

One alone or two or more different types of electron transport materials may be used in one layer either singly or as suitably selected and combined. The electron injection layer and the electron, transport layer may be formed, for example, according to a vapor deposition method, a sputtering method or a coating method. The thickness of the electron injection layer and the electron transport layer may be generally at least 3 nm each, preferably at least 10 nm each. The upper limit may be, for example, at most 5 μm each.

(Cathode)

The cathode has a function of injecting electrons toward the organic layer. As the cathode, preferably used is a material having a low work function. For example, a material having a work function of at most 4 eV is preferably used. Concretely, there are mentioned metals (for example, tin, magnesium, indium, calcium, aluminium, silver), and alloys (for example, aluminium-lithium alloy, magnesium-silver alloy, magnesium-indium alloy). In case where emitted light is taken out from the side of the cathode, preferred is use of a material having a high light transmittance. The transmittance is preferably at least 10%, more preferably at least 50%, even more preferably at least 80%. The thickness of the cathode is generally at least 3 nm, but preferably at least 10 nm. The upper limit may be, for example, at most 1 μm, however, when the cathode is not required to have transparency, the thickness thereof may be further larger. The cathode may be formed, for example, according to a vapor deposition method, a sputtering method, or a coating method. Preferably, a protective layer is formed on the cathode for protecting the cathode. The protective layer of the type is preferably a layer formed of a metal that has a high work function and is stable. For example, a metal layer of aluminium, silver, copper, nickel, chromium, gold, platinum or the like may be formed.

The organic electroluminescence element of the invention is applicable to a variety of uses. For example, using the organic electroluminescence element of the invention, it is possible to produce organic electroluminescence display devices. For the details, referred to is "Organic EL Display" written by Shizuo Tokito, Chihaya Adachi, Yukihide Murata (Ohm Publishing). In particular, the organic electroluminescence element of the invention is applicable to organic electroluminescence lighting that is much in demand.

EXAMPLES

The characteristics of the invention are described more concretely with reference to the following Synthesis Examples, Test Examples and Production Examples. In the following Examples, the materials used, the details of the treatment and the treatment process may be suitably modified or changed not overstepping the spirit and the scope of the invention. Accordingly, the scope of the invention should not be limitatively interpreted by the Examples mentioned below.

Synthesis Example 1

Compound 1 was synthesized according to the following scheme in this Synthesis Example.

[Chem. 25]

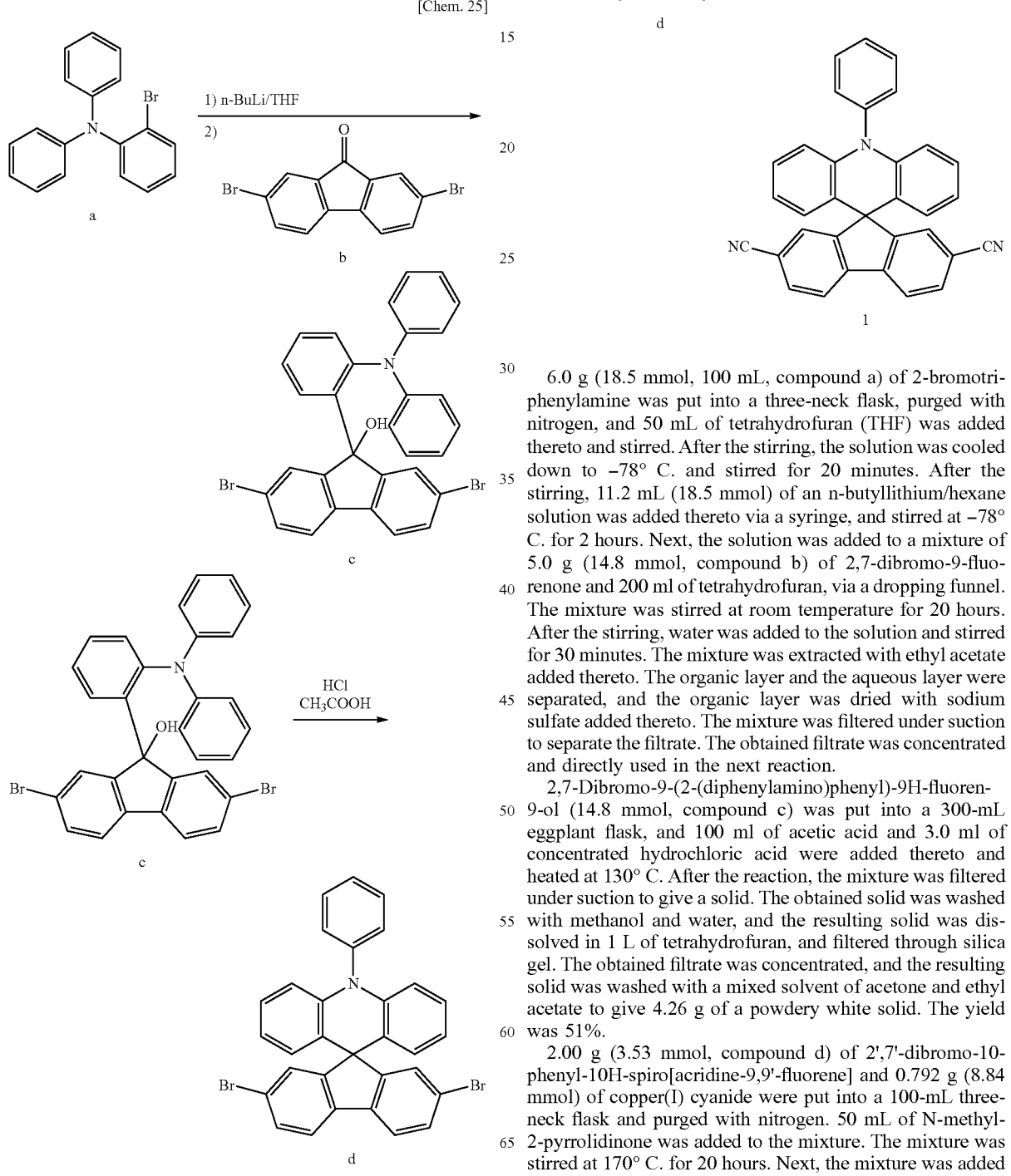

6.0 g (18.5 mmol, 100 mL, compound a) of 2-bromotriphenylamine was put into a three-neck flask, purged with nitrogen, and 50 mL of tetrahydrofuran (THF) was added thereto and stirred. After the stirring, the solution was cooled down to −78° C. and stirred for 20 minutes. After the stirring, 11.2 mL (18.5 mmol) of an n-butyllithium/hexane solution was added thereto via a syringe, and stirred at −78° C. for 2 hours. Next, the solution was added to a mixture of 5.0 g (14.8 mmol, compound b) of 2,7-dibromo-9-fluorenone and 200 ml of tetrahydrofuran, via a dropping funnel. The mixture was stirred at room temperature for 20 hours. After the stirring, water was added to the solution and stirred for 30 minutes. The mixture was extracted with ethyl acetate added thereto. The organic layer and the aqueous layer were separated, and the organic layer was dried with sodium sulfate added thereto. The mixture was filtered under suction to separate the filtrate. The obtained filtrate was concentrated and directly used in the next reaction.

2,7-Dibromo-9-(2-(diphenylamino)phenyl)-9H-fluoren-9-ol (14.8 mmol, compound c) was put into a 300-mL eggplant flask, and 100 ml of acetic acid and 3.0 ml of concentrated hydrochloric acid were added thereto and heated at 130° C. After the reaction, the mixture was filtered under suction to give a solid. The obtained solid was washed with methanol and water, and the resulting solid was dissolved in 1 L of tetrahydrofuran, and filtered through silica gel. The obtained filtrate was concentrated, and the resulting solid was washed with a mixed solvent of acetone and ethyl acetate to give 4.26 g of a powdery white solid. The yield was 51%.

2.00 g (3.53 mmol, compound d) of 2',7'-dibromo-10-phenyl-10H-spiro[acridine-9,9'-fluorene] and 0.792 g (8.84 mmol) of copper(I) cyanide were put into a 100-mL three-neck flask and purged with nitrogen. 50 mL of N-methyl-2-pyrrolidinone was added to the mixture. The mixture was stirred at 170° C. for 20 hours. Next, the mixture was added to an aqueous sodium hydroxide solution and stirred, and an aqueous sodium hypochlorite solution was added thereto and further stirred for 30 minutes. The mixture was dissolved in toluene, then the aqueous layer and the organic layer were separated from each other, and the organic layer was washed with water. The organic layer was dried with magnesium sulfate. The obtained mixture was filtered under suction to give a filtrate. Further, the obtained filtrate was concentrated and purified through silica gel column chromatography. In the column chromatography, toluene/hexane=1/2 was used as the developing solvent, and then toluene and toluene/ethyl acetate=50/1 mixed solvent were further used as the developing solvents. The obtained fraction was concentrated, and the resulting solid was dissolved in chloroform and separated through GPC. The solid obtained through concentration of the fraction was recrystallized from a mixed solvent of acetone and methanol to give 0.81 g of a needle-like yellow solid (compound 1). The yield was 50%. The compound was identified through $^1$H-NMR, $^{13}$C-NMR, TOF-Mass and elementary analysis.

$^1$H-NMR (500 MHz, CDCl$_3$, TMS, δ): 6.26 (dd, J=7.8 Hz, 1.5 Hz, 2H), 6.42 (dd, J=8.4 Hz, 0.8 Hz, 2H), 6.62 (td, J=7.4 Hz, 1.1 Hz, 2H), 7.01 (td, J=7.8 Hz, 1.5 Hz, 2H), 7.49 (d, J=7.8 Hz, 2H), 7.61 (t, J=7.5 Hz, 1H), 7.73-7.76 (m, 6H), 7.94 (d, J=8.3 Hz, 2H)

$^{13}$C-NMR (125 MHz, CDCl$_3$, δ): 157.49, 141.50, 141.12, 140.30, 132.20, 131.32, 130.91, 129.97, 128.87, 128.36, 127.11, 121.62, 121.29, 120.96, 118.72, 115.48, 113.20, 57.25

TOF-Mass [M$^+$]: Anal. Calcd for C$_{33}$H$_{19}$N$_3$: 458.16; Found: 458.24.

Elementary Analysis: Anal. Calcd for C$_{33}$H$_{19}$N$_3$: C, 86.63, H, 4.19, N, 9.18%; Found: C, 86.82, H, 4.23, N, 9.16%.

Synthesis Examples 2 to 282 and 284 to 354

In the same manner as in Synthesis Example 1, compounds 2 to 282 and 284 to 354 can be produced.

Synthesis Example 283

Compound 283 was synthesized according to the following scheme in this Synthesis Example.

[Chem. 26]

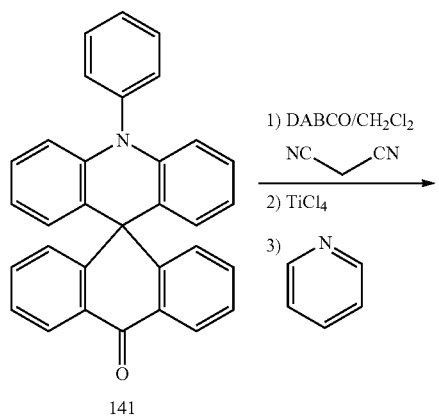

141

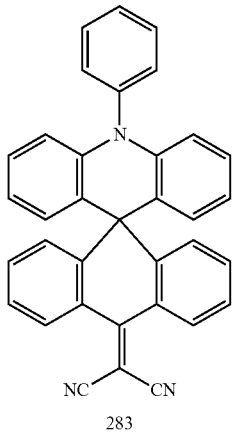

283

1.5 g (3.4 mmol, compound 141) of 10-phenyl-[spiroacridine-9(10H), 9'(10'H)anthracen]-10'-one and 3.9 g (34 mmol) of 1,4-diazabicyclo[2.2.2]octane (abbreviation: DABCO), both known compounds, were put into a 100-mL three-neck flask, and purged with nitrogen. 60 mL of dichloromethane was added to the mixture and stirred. After the stirring, 2.3 g (34 mmol) of malononitrile was added thereto, and then 6.5 g (34 mmol) of titanium tetrachloride was added thereto little by little. 2.7 g (34 mmol) of pyridine was added to the mixture little by little, and in a nitrogen stream atmosphere, this was stirred at room temperature for 20 hours. After the stirring, water was added to the mixture and further stirred. After the stirring, the mixture was extracted with chloroform added thereto. After the extraction, the organic layer and the aqueous layer were separated from each other, and the organic layer was washed with saturated saline water. After the washing, the organic layer was dried with magnesium sulfate added thereto. After the drying, the mixture was filtered under suction to separate the filtrate. The obtained filtrate was concentrated, and the resulting solid was purified through silica gel column chromatography. In the column chromatography, the developing solvent used was a mixed solvent of dichloromethane/hexane=1/1.

The obtained fraction was concentrated, and ethanol was added to the resulting solid and irradiated with ultrasonic waves. After the irradiation, the solid was collected to be 0.15 g of a pale orange powdery solid (compound 283). The yield was 9.0%.

$^1$H-NMR (500 MHz, CDCl$_3$, TMS, δ): 8.25 (d, J=8.0 Hz, 2H), 7.72 (t, J=7.3 Hz, 2H), 7.59 (t, J=7.5 Hz, 1H), 7.49-7.41 (m, 8H), 6.94 (t, J=7.8 Hz, 2H), 6.65 (t, J=7.5 Hz, 2H), 6.39-6.34 (m, 4H).

MS (MALDI): m/z calcd: 483.17 [M+H]$^+$; found: 483.08.

Example 1

In this Example, the compound 1 produced in Synthesis Example 1 was used for the test, and an organic electroluminescence element having the configuration shown in FIG. 1 was produced.

(1) Observation of Delayed Fluorescence

Figure 2:
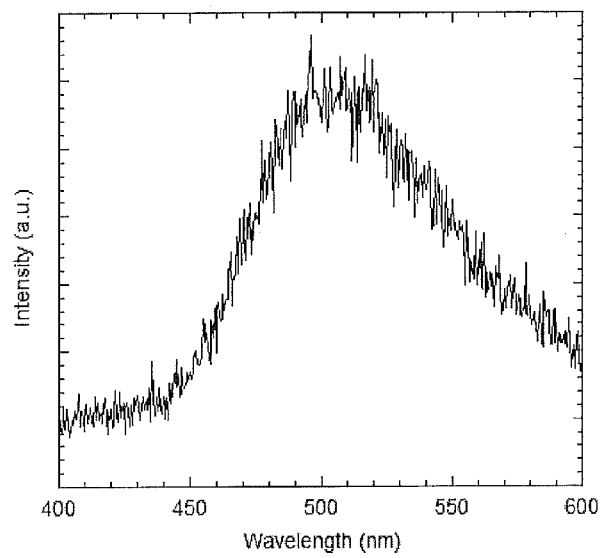
FIG. 2 This is a photoluminescence spectrum in Example 1.
Figure 3:
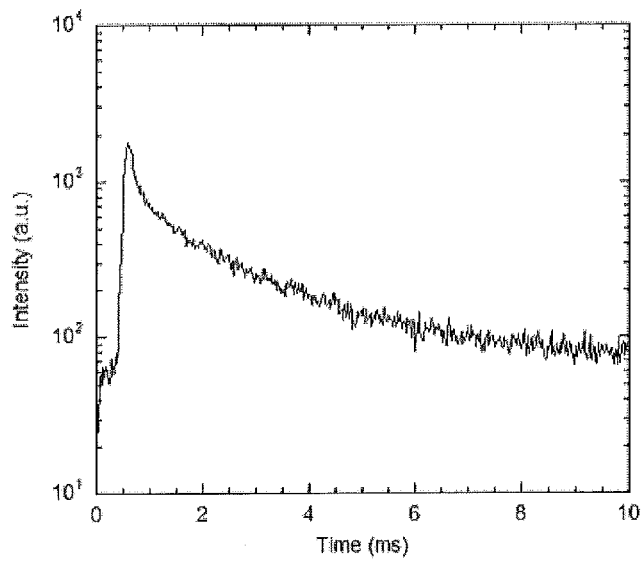
FIG. 3 This is a graph showing the PL transient decay in Example 1.

A film was formed on a quartz substrate by co-deposition of 10 wt % compound 1 and mCP, and analyzed for the photoluminescence spectrum, the PL quantum yield and the PL transient decay thereof. FIG. 2 shows the photoluminescence spectrum at an excitation wavelength of 339 nm. The co-deposition film gave green emission, and the PL quantum yield thereof was 35% and was high. Next, for investigating the thermally-activated delayed fluorescence characteristic of the compound 1, the co-deposition film was analyzed for the PL transient decay thereof using a streak camera. The measured results are shown in FIG. 3. The PL transient decay curve well corresponded to the fitting of the two components, and showed a short-life component of 18 ns and a long-life component of 5.2 ms. Specifically, owing to the presence of the compound 1 therein, the film gave the thermally-activated delayed fluorescence derived from the long-life component in addition to the short-life fluorescence.

(2) Production of Organic Electroluminescence Element 1

On the glass 1, a film of indium/tin oxide (ITO) 2 was formed in a thickness of approximately from 30 to 100 nm, and a film of mCP 3 was further formed thereon in a thickness of 60 nm. Next, 6 wt % compound 1 and mCP were co-deposited to form a light-emitting layer 4 in a thickness of 20 nm. Further on this, a film of Bphen 5 was formed in a thickness of 40 nm. Next, a film of magnesium-silver (MgAg) 6 was vacuum-deposited in a thickness of 100 nm, and then aluminium (Al) 7 was deposited thereon in a thickness of 20 nm, thereby producing an organic electroluminescence element having the configuration shown in FIG. 1. Thus formed, the organic EL element gave a green emission well conforming to the corresponding PL spectrum, which therefore confirmed that the emission from the element was derived from the compound 1.

(3) Production of Organic Electroluminescence Element 2

Figure 4:
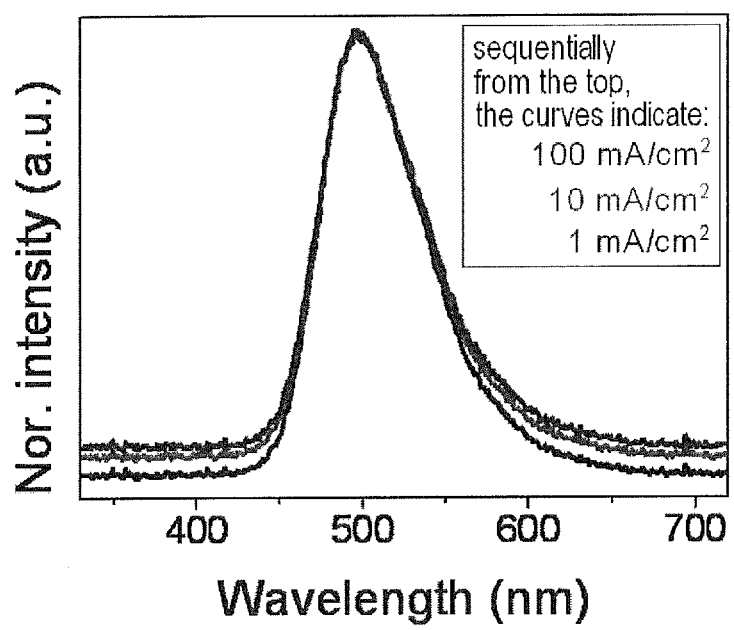
FIG. 4 This is an electroluminescence (EL) spectrum of the organic electroluminescence element of Example 1.
Figure 5:
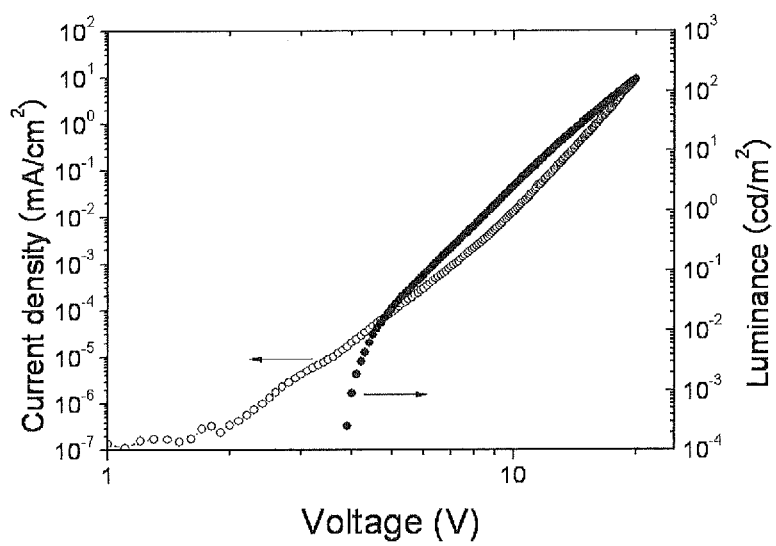
FIG. 5 This is a graph showing the current density-voltage characteristic-luminance characteristic of the organic electroluminescence element of Example 1.
Figure 6:
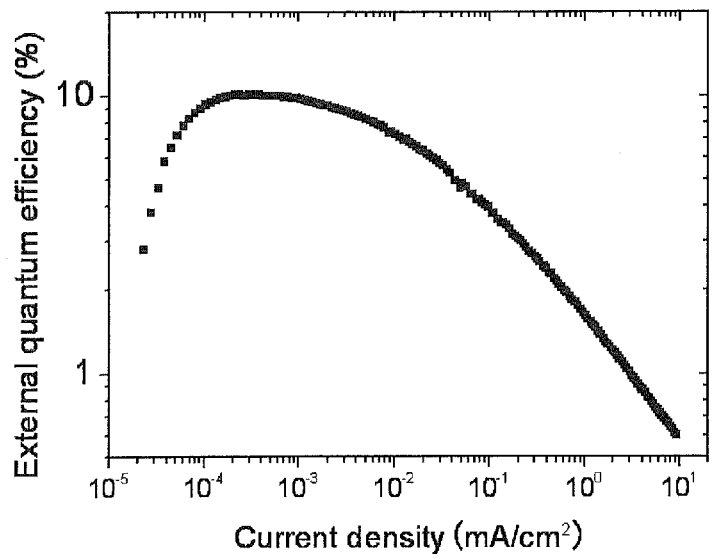
FIG. 6 This is a graph showing the external quantum efficiency-current density characteristic of the organic electroluminescence element of Example 1.

On glass, a film of indium/tin oxide (ITO) was formed in a thickness of approximately from 30 to 100 nm, and a film of TAPC was formed thereon in a thickness of 40 nm and a film of mCP was further thereon in a thickness of 5 nm. Next, 6 wt % compound 1 and TPSi-F were co-deposited to form a light-emitting layer in a thickness of 20 nm. Further on this, a film of TmPyPB was formed in a thickness of 35 nm. Next, lithium fluoride (LiF) was vacuum-deposited thereon in a thickness of 1 nm, and then aluminium (Al) was deposited thereon in a thickness of 60 nm, thereby producing an organic electroluminescence element. FIG. 4 shows the electroluminescence (EL) spectrum of the element. FIG. 5 shows the current density-voltage characteristic-luminance characteristic of the element, and FIG. 6 shows the external quantum efficiency-current density characteristic thereof. It was confirmed that the external quantum efficiency was 10% and was high.

[Chem. 27]

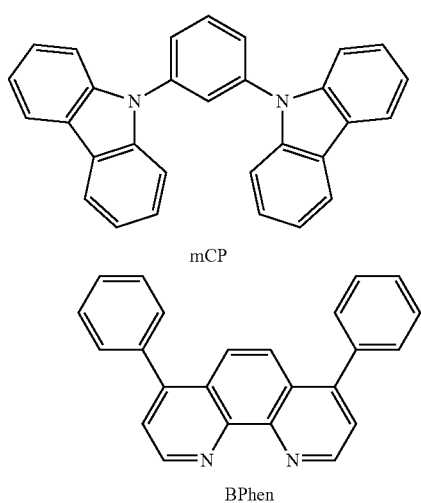

mCP

BPhen

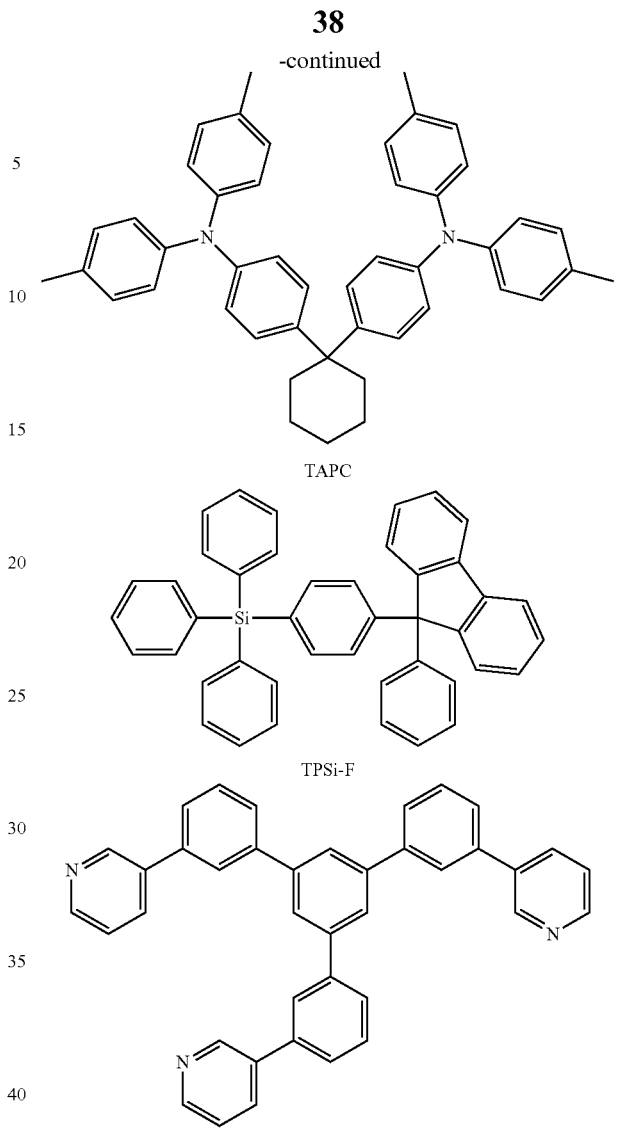

TAPC

TPSi-F

TmPyPB

Examples 2 to 140

In the same manner as in Example 1, the usefulness of the compounds 2 to 140 and 142 to 354 can also be confirmed.

Example 141

In this Example, the compound 141 was used and tested in the same manner as in Example 1, and an organic electroluminescence element was produced.

(1) Observation of Delayed Fluorescence

Figure 7:
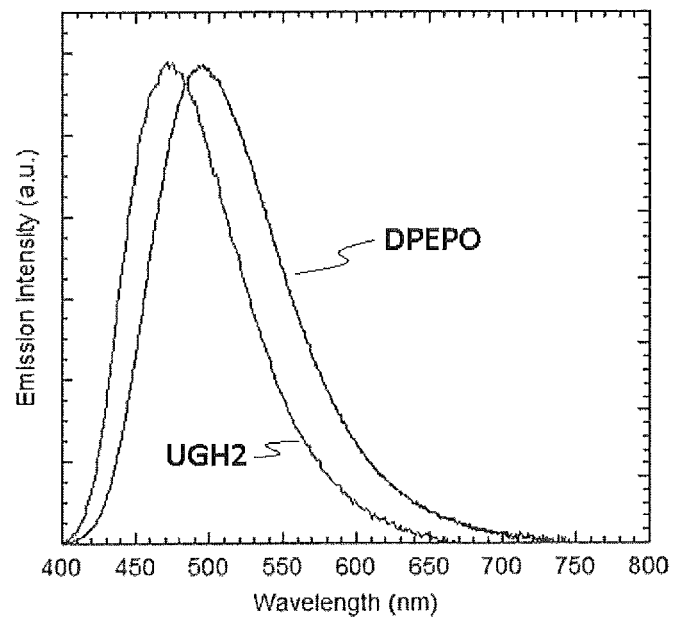
FIG. 7 This is a photoluminescence spectrum in Example 141.
Figure 8:
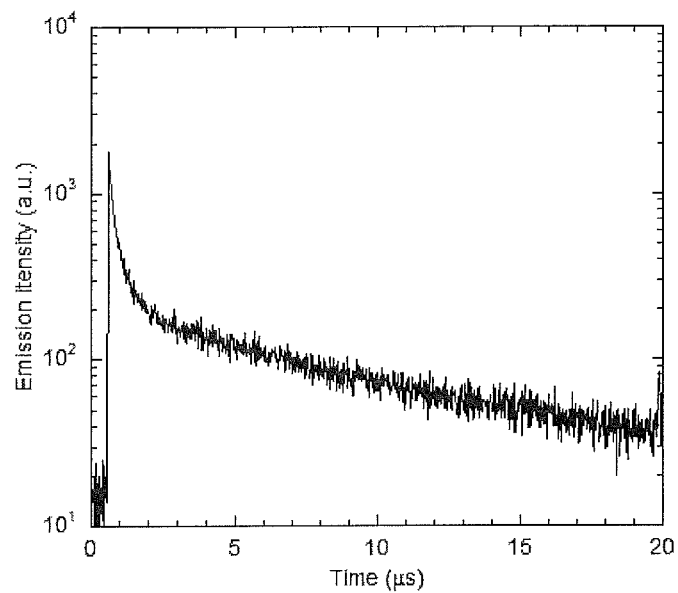
FIG. 8 This is a graph showing the PL transient decay in Example 141.

A film was formed on a quartz substrate by co-deposition of 10 wt % compound 141 and DPEPO or UGH2, and analyzed in the same manner as in Example 1 for the photoluminescence spectrum, the PL quantum yield and the PL transient decay thereof. FIG. 7 shows the photoluminescence spectrum at an excitation wavelength of 339 nm. FIG. 8 shows the PL transient decay curve. Owing to the presence of the compound 141 therein, the film gave the thermally-activated delayed fluorescence derived from the long-life component in addition to the short-life fluorescence. The PL quantum yield was 74 in co-deposition with DPEPO and was 80% in co-deposition with UGH2, and both were high.

(2) Production of Organic Electroluminescence Element

Figure 9:
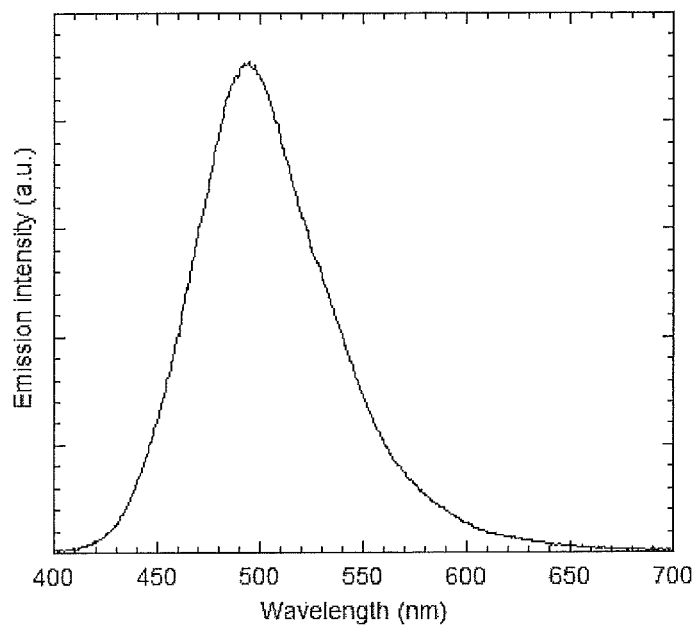
FIG. 9 This is an electroluminescence (EL) spectrum of the organic electroluminescence element of Example 141.
Figure 10:
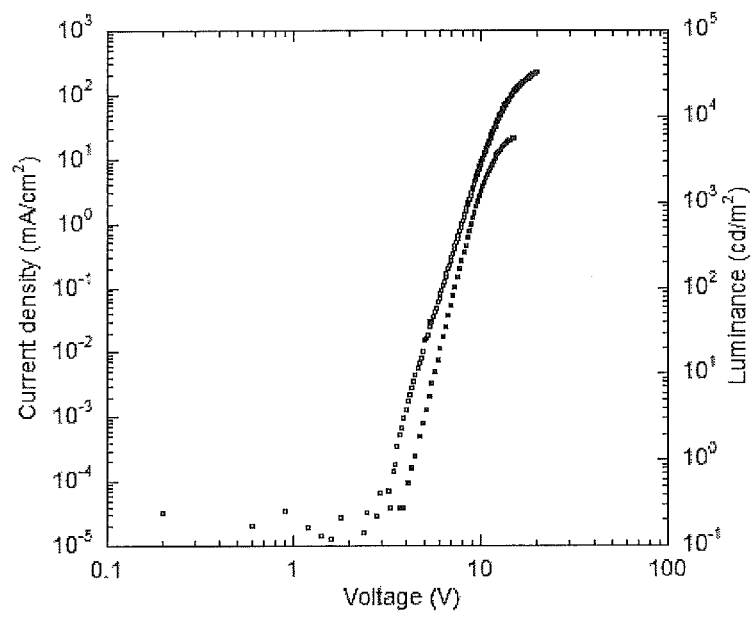
FIG. 10 This is a graph showing the current density-voltage characteristic-luminance characteristic of the organic electroluminescence element of Example 141.
Figure 11:
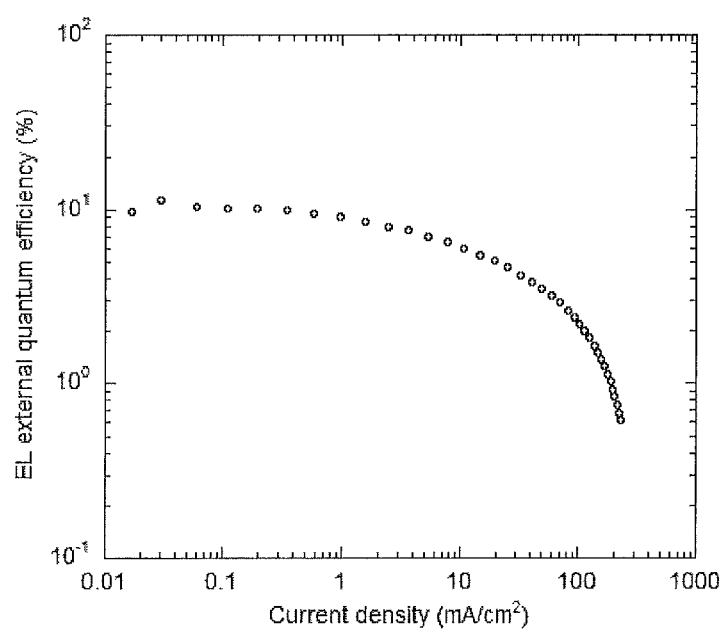
FIG. 11 This is a graph showing the external quantum efficiency-current density characteristic of the organic electroluminescence element of Example 141.

On glass, a film of indium/tin oxide (ITO) was formed in a thickness of approximately 100 nm, and a film of NPD was formed thereon in a thickness of 40 nm and a film of mCP was further thereon in a thickness of 10 nm. Next, 9 wt % compound 141 and DPEPO were co-deposited to form a light-emitting layer in a thickness of 40 nm. Further on this, a film of DPEPO was formed in a thickness of 20 nm. Next, magnesium-silver (MgAg=10/1) was vacuum-deposited thereon in a thickness of 100 nm, and then aluminium (Al) was deposited thereon in a thickness of 10 nm, thereby producing an organic electroluminescence element. FIG. 9 shows the electroluminescence (EL) spectrum of the element. This well conformed to the corresponding PL spectrum, which therefore confirmed that the emission from the element was derived from the compound 141. FIG. 10 shows the current density-voltage characteristic-luminance characteristic of the element, and FIG. 11 shows the external quantum efficiency-current density characteristic thereof. It was confirmed that the external quantum efficiency was 10.7% and was high.

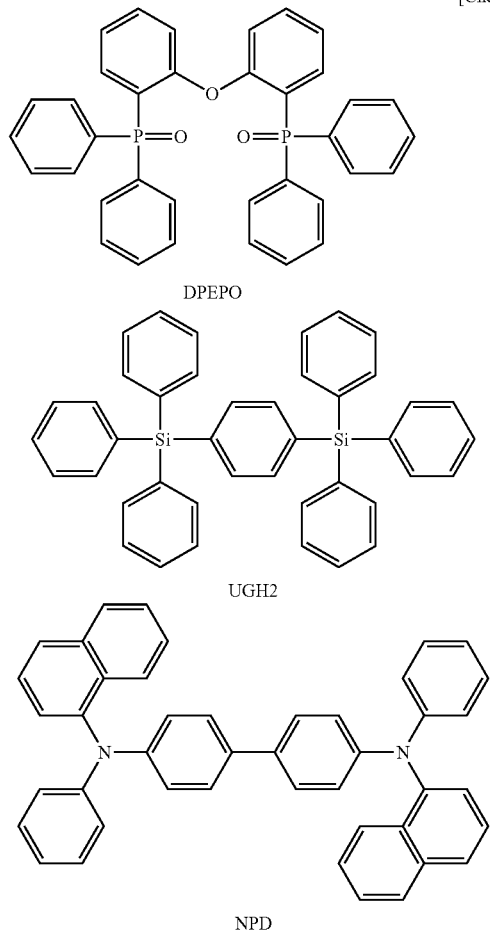

[Chem. 28]

DPEPO

UGH2

NPD

INDUSTRIAL APPLICABILITY

The organic electroluminescence element of the invention can be produced at a low cost, and can realize a high emission efficiency. In addition, the compound of the invention is useful as a light-emitting material for such organic electroluminescence elements. Consequently, the industrial applicability of the invention is great.

REFERENCE SIGNS LIST

1 Glass
2 ITO
3 mCP
4 Light-Emitting Layer
5 Bphen
6 MgAg
7 Al

The invention claimed is:

1. An organic electroluminescence element having an anode, a cathode, and at least one organic layer containing a light-emitting layer between the anode and the cathode, wherein the light-emitting layer contains a compound represented by the following general formula (1):

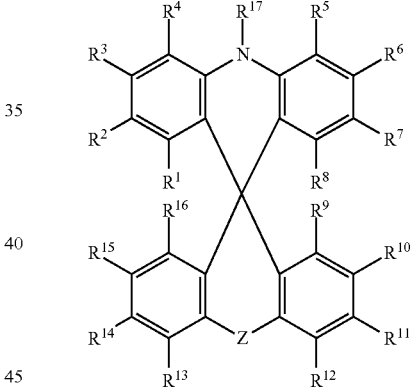

General Formula (1)

wherein, in the general formula (1), $R^1$, $R^2$, $R^3$, $R^4$, $R^5$, $R^6$, $R^7$, $R^8$ and $R^{17}$ each independently represent a hydrogen atom or an electron-donating group, and at least one of $R^1$, $R^2$, $R^3$, $R^4$, $R^5$, $R^6$, $R^7$, $R^8$ or $R^{17}$ is an electron-donating group; $R^9$, $R^{10}$, $R^{11}$, $R^{12}$, $R^{13}$, $R^{14}$, $R^{15}$ and $R^{16}$ each independently represent a hydrogen atom, or an electron-withdrawing group that does not have an unshared electron pair at the α-position thereof; Z represents >C=Y, Y represents $C(CN)_2$.

2. An organic electroluminescence element having an anode, a cathode, and at least one organic layer containing a light-emitting layer between the anode and the cathode, wherein the light-emitting layer contains a compound represented by the following general formula (1), which radiates delayed fluorescence:

General Formula (1)

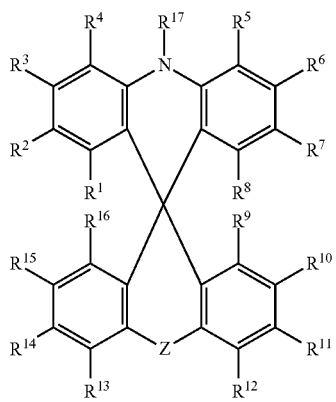

wherein, in the general formula (1), $R^1$, $R^2$, $R^3$, $R^4$, $R^5$, $R^6$, $R^7$, $R^8$ and $R^{17}$ each independently represent a hydrogen atom or an electron-donating group, and at least one of $R^1$, $R^2$, $R^3$, $R^4$, $R^5$, $R^6$, $R^7$, $R^8$ or $R^{17}$ is an electron-donating group; $R^9$, $R^{10}$, $R^{11}$, $R^{12}$, $R^{13}$, $R^{14}$, $R^{15}$ and $R^{16}$ each independently represent a hydrogen atom, or an electron-withdrawing group that does not have an unshared electron pair at the α-position thereof; Z represents >C=Y, and Y represents O or $C(CN)_2$.

3. The organic electroluminescence element according to claim 2, wherein Z in the general formula (1) is a carbonyl group.

4. The organic electroluminescence element according to claim 1, wherein $R^{17}$ in the general formula (1) is an aryl group.

5. The organic electroluminescence element according to claim 1, wherein at least one of $R^1$, $R^2$, $R^3$, $R^4$, $R^5$, $R^6$, $R^7$ or $R^8$ in the general formula (1) is an aryl group substituted with an electron-donating group.

6. The organic electroluminescence element according to claim 1, wherein at least one of $R^1$, $R^2$, $R^3$, $R^4$, $R^5$, $R^6$, $R^7$ or $R^8$ in the general formula (1) has a structure represented by the following general formula (2):

General Formula (2)

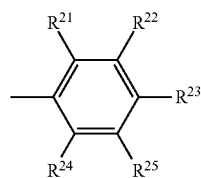

wherein, in the general formula (2), $R^{21}$, $R^{22}$, $R^{23}$, $R^{24}$ and $R^{25}$ each independently represent a hydrogen atom or an electron-donating group, and at least one of $R^{21}$, $R^{22}$, $R^{23}$, $R^{24}$ or $R^{25}$ is an electron-donating group.

7. The organic electroluminescence element according to claim 1, wherein at least one of $R^1$, $R^2$, $R^3$, $R^4$, $R^5$, $R^6$, $R^7$ or $R^8$ in the general formula (1) has a structure represented by any of the following general formulae (3) to (5):

General Formula (3)

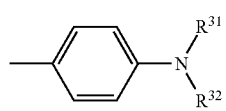

General Formula (4)

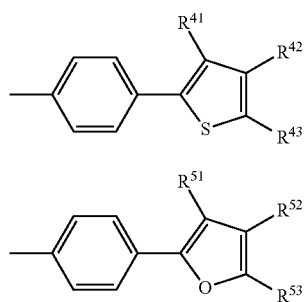

General Formula (5)

wherein, in the above formulae, $R^{31}$ and $R^{32}$ each independently represent a substituted or unsubstituted aryl group; and the aryl group represented by $R^{31}$ may bond to the aryl group represented by $R^{32}$; $R^{41}$, $R^{42}$ and $R^{43}$ each independently represent a hydrogen atom, a substituted or unsubstituted alkyl group, or a substituted or unsubstituted aryl group; $R^{41}$ and $R^{42}$ may together form a cyclic structure, and $R^{42}$ and $R^{43}$ may together form a cyclic structure; $R^{51}$, $R^{52}$ and $R^{53}$ each independently represent a hydrogen atom, a substituted or unsubstituted alkyl group, or a substituted or unsubstituted aryl group; $R^{51}$ and $R^{52}$ may together form a cyclic structure, and $R^{52}$ and $R^{53}$ may together form a cyclic structure.

8. The organic electroluminescence element according to claim 1, wherein at least one of $R^1$, $R^2$, $R^3$, $R^4$, $R^5$, $R^6$, $R^7$ or $R^8$ in the general formula (1) has any of the following structures:

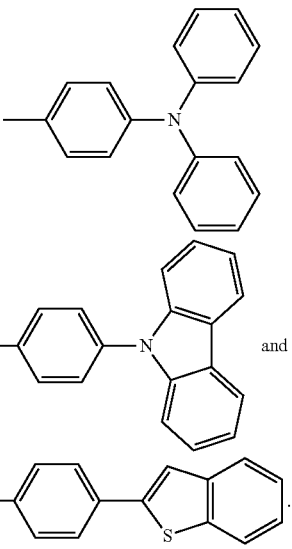

9. The organic electroluminescence element according to claim 1, wherein at least one of $R^9$, $R^{10}$, $R^{11}$, $R^{12}$, $R^{13}$, $R^{14}$, $R^{15}$ or $R^{16}$ is a cyano group or has a structure represented by any of the following general formulae (6) to (9):

General Formula (6)

$$-P\!\!\begin{array}{c}R^{61}\\\parallel\\R^{62}\end{array}\!\!=\!O$$

General Formula (7)

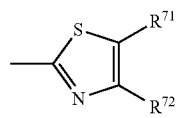

General Formula (8)

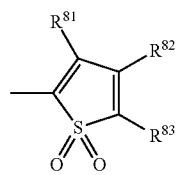

General Formula (9)

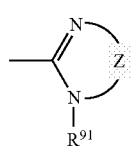

wherein, in the above formulae, $R^{61}$ and $R^{62}$ each independently represent a substituted or unsubstituted aryl group; $R^{71}$ and $R^{72}$ each independently represent a hydrogen atom, a substituted or unsubstituted alkyl group, or a substituted or unsubstituted aryl group; and $R^{71}$ and $R^{72}$ may together form a cyclic structure; $R^{81}$, $R^{82}$ and $R^{83}$ each independently represent a hydrogen atom, a substituted or unsubstituted alkyl group, or a substituted or unsubstituted aryl group; $R^{81}$ and $R^{82}$ may together form a cyclic structure, and $R^{82}$ and $R^{83}$ may together form a cyclic structure; $R^{91}$ represents a hydrogen atom, a substituted or unsubstituted alkyl group, or a substituted or unsubstituted aryl group; and Z represents a linking group necessary for forming a heteroaromatic ring.

10. The organic electroluminescence element according to claim 1, wherein at least one of $R^9$, $R^{10}$, $R^{11}$, $R^{12}$, $R^{13}$, $R^{14}$, $R^{15}$ or $R^{16}$ in the general formula (1) has any of the following structures:

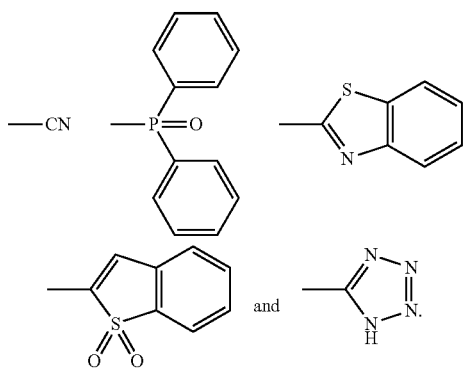

11. An organic electroluminescence element, wherein a compound represented by the following general formula (1) is used as a dopant in a light-emitting layer General Formula (1)

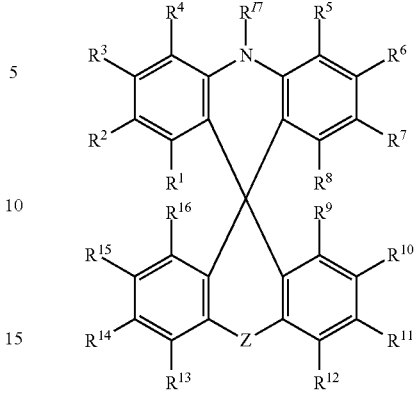

wherein, in the general formula (1), $R^1$, $R^2$, $R^3$, $R^4$, $R^5$, $R^6$, $R^7$, $R^8$ and $R^{17}$ each independently represent a hydrogen atom or an electron-donating group, and at least one of $R^1$, $R^2$, $R^3$, $R^4$, $R^5$, $R^6$, $R^7$, $R^8$ or $R^{17}$ is an electron-donating group; $R^9$, $R^{10}$, $R^{11}$, $R^{12}$, $R^{13}$, $R^{14}$, $R^{15}$ and $R^{16}$ each independently represent a hydrogen atom, or an electron-withdrawing group that does not have an unshared electron pair at the α-position thereof; Z represents >C=Y, and Y represents O or $C(CN)_2$.

12. A compound represented by the following general formula (1'):

General Formula (1')

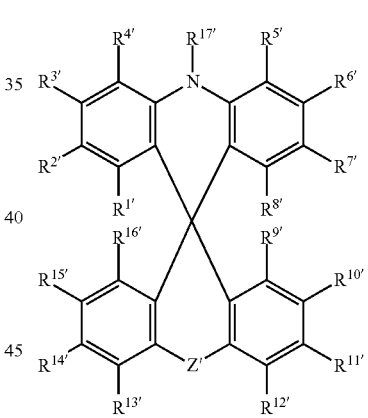

wherein, in the general formula (1'), $R^{1'}$, $R^{2'}$, $R^{3'}$, $R^{4'}$, $R^{5'}$, $R^{6'}$, $R^{7'}$, $R^{8'}$, and $R^{17'}$ each independently represent a hydrogen atom or an electron-donating group, and at least one of $R^{1'}$, $R^{2'}$, $R^{3'}$, $R^{4'}$, $R^{5'}$, $R^{6'}$, $R^{7'}$, $R^{8'}$ or $R^{17'}$ is an electron-donating group; $R^{9'}$, $R^{10'}$, $R^{11'}$, $R^{12'}$, $R^{13'}$, $R^{14'}$, $R^{15'}$ and $R^{16'}$ each independently represent a hydrogen atom or a cyano group; Z' represents >C=Y, and Y represents O or $C(CN)_2$.

13. The compound according to claim 12, wherein Z' in the general formula (1') is a carbonyl group.

14. The compound according to claim 12, wherein Z' in the general formula (1') is >C=$C(CN)_2$.

15. The compound according to claim 12, wherein $R^{17'}$ in the general formula (1') is an aryl group.

16. The compound according to claim 12, wherein at least one of $R^{1'}$, $R^{2'}$, $R^{3'}$, $R^{4'}$, $R^{5'}$, $R^{6'}$, $R^{7'}$ or $R^{8'}$ in the general formula (1') is an aryl group substituted with an electron-donating group.

17. The compound according to claim 12, wherein at least one of $R^{1'}$, $R^{2'}$, $R^{3'}$, $R^{4'}$, $R^{5'}$, $R^{6'}$, $R^{7'}$ or $R^{8'}$ in the general formula (1') has a structure represented by the following general formula (2):

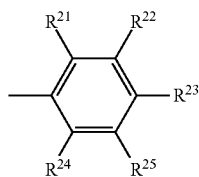

General Formula (2)

wherein, in the general formula (2), $R^{21}$, $R^{22}$, $R^{23}$, $R^{24}$ and $R^{25}$ each independently represent a hydrogen atom or an electron-donating group, and at least one of $R^{21}$, $R^{22}$, $R^{23}$, $R^{24}$ or $R^{25}$ is an electron-donating group.

18. The compound according to claim 12, wherein at least one of $R^{1'}$, $R^{2'}$, $R^{3'}$, $R^{4'}$, $R^{5'}$, $R^{6'}$, $R^{7'}$, or $R^{8'}$ in the general formula (1') has a structure represented by any of the following general formulae (3) to (5):

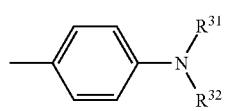

General Formula (3)

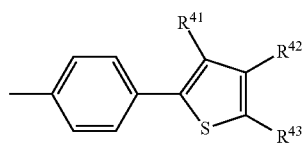

General Formula (4)

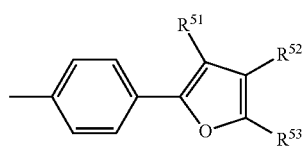

General Formula (5)

wherein, in the above formulae, $R^{31}$ and $R^{32}$ each independently represent a substituted or unsubstituted aryl group; and the aryl group represented by $R^{31}$ may bond to the aryl group represented by $R^{32}$; $R^{41}$, $R^{42}$ and $R^{43}$ each independently represent a hydrogen atom, a substituted or unsubstituted alkyl group, or a substituted or unsubstituted aryl group; $R^{41}$ and $R^{42}$ may together form a cyclic structure, and $R^{42}$ and $R^{43}$ may together form a cyclic structure; $R^{51}$, $R^{52}$ and $R^{53}$ each independently represent a hydrogen atom, a substituted or unsubstituted alkyl group, or a substituted or unsubstituted aryl group; $R^{51}$ and $R^{52}$ may together form a cyclic structure, and $R^{52}$ and $R^{53}$ may together form a cyclic structure.

19. The compound according to claim 12, wherein at least one of $R^{1'}$, $R^{2'}$, $R^{3'}$, $R^{4'}$, $R^{5'}$, $R^{6'}$, $R^{7'}$ or $R^{8'}$ in the general formula (1') has any of the following structures:

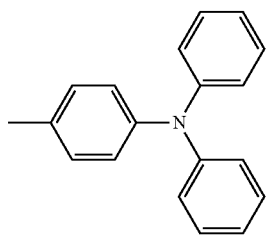

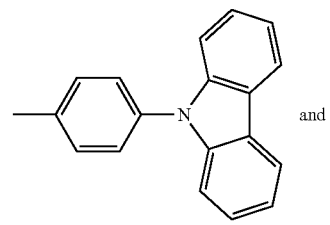

and

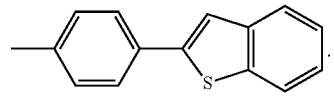

20. A delayed fluorescence emitter having a structure represented by the following general formula (1):

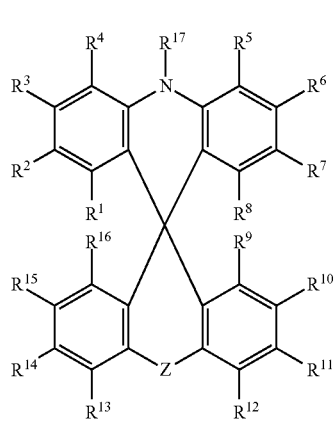

General Formula (1)

wherein, in the general formula (1), $R^1$, $R^2$, $R^3$, $R^4$, $R^5$, $R^6$, $R^7$, $R^8$ and $R^{17}$ each independently represent a hydrogen atom or an electron-donating group, and at least one of $R^1$, $R^2$, $R^3$, $R^4$, $R^5$, $R^6$, $R^7$, $R^8$ or $R^{17}$ is an electron-donating group; $R^9$, $R^{10}$, $R^{11}$, $R^{12}$, $R^{13}$, $R^{14}$, $R^{15}$ and $R^{16}$ each independently represent a hydrogen atom, or an electron-withdrawing group that does not have an unshared electron pair at the α-position thereof; Z represents >C=Y, and Y represents O or $C(CN)_2$.

21. A delayed fluorescence material comprising a compound represented by the following general formula (1'):

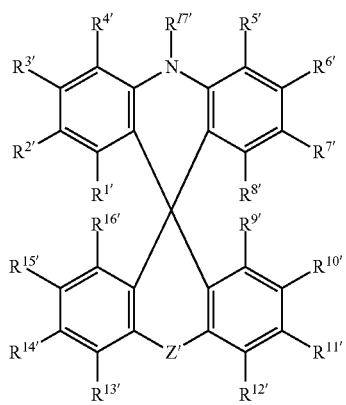

General Formula (1')

wherein, in the general formula (1'), $R^{1'}$, $R^{2'}$, $R^{3'}$, $R^{4'}$, $R^{5'}$, $R^{6'}$, $R^{7'}$, $R^{8'}$ and $R^{17'}$ each independently represent a hydrogen atom or an electron-donating group, and at least one of tR$^{1'}$, $R^{2'}$, $R^{3'}$, $R^{4'}$, $R^{5'}$, $R^{6'}$, $R^{7'}$, $R^{8'}$ or $R^{17'}$ is an electron donating group; $R^{9'}$, $R^{10'}$, $R^{11'}$, $R^{12'}$, $R^{13'}$, $R^{14'}$, $R^{15'}$ and $R^{16'}$ each independently represent a hydrogen atom or a cyano group; Z' represents >C=Y, and Y represents O or $C(CN)_2$.

22. In a method of providing delayed fluorescence or luminescence, comprising subjecting an electroluminescence element to a light inducing stimulus, the improvement wherein the electroluminescence element comprises a delayed fluorescence emitter:

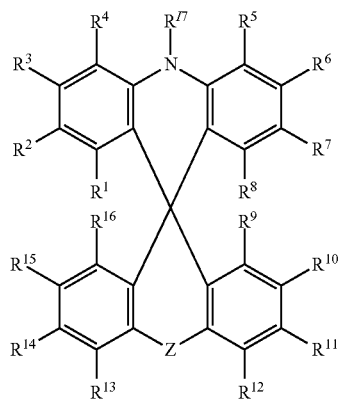

General Formula (1)

wherein, in the general formula (1), $R^1$, $R^2$, $R^3$, $R^4$, $R^5$, $R^6$, $R^7$, $R^8$ and $R^{17}$ each independently represent a hydrogen atom or an electron-donating group, and at least one of $R^1$, $R^2$, $R^3$, $R^4$, $R^5$, $R^6$, $R^7$, $R^8$ or $R^{17}$ is an electron-donating group; $R^9$, $R^{10}$, $R^{11}$, $R^{12}$, $R^{13}$, $R^{14}$, $R^{15}$ and $R^{16}$ each independently represent a hydrogen atom, or an electron-withdrawing group that does not have an unshared electron pair at the α-position thereof; Z represents >C=Y, and Y represents O or $C(CN)_2$.

23. A light-emitting material comprising a compound represented by the following general formula (1):

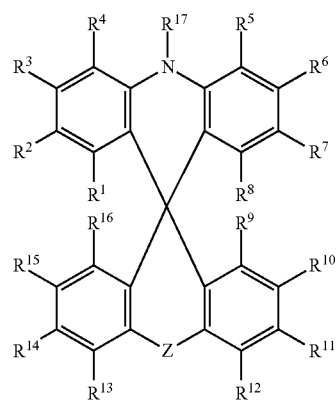

General Formula (1)

wherein, in the general formula (1), $R^1$, $R^2$, $R^3$, $R^4$, $R^5$, $R^6$, $R^7$, $R^8$ and $R^{17}$ each independently represent a hydrogen atom or an electron-donating group, and at least one of $R^1$, $R^2$, $R^3$, $R^4$, $R^5$, $R^6$, $R^7$, $R^8$ or $R^{17}$ is an electron-donating group; $R^9$, $R^{10}$, $R^{11}$, $R^{12}$, $R^{13}$, $R^{14}$, $R^{15}$ and $R^{16}$ each independently represent a hydrogen atom, or an electron-withdrawing group that does not have an unshared electron pair at the α-position thereof; Z represents >C=Y, and Y represents O or $C(CN)_2$.

24. In an organic electroluminescence display device comprising an organic electroluminescence element, wherein the improvement comprises that the organic electroluminescence element is in accordance with claim 11.

* * * * *